United States Patent
Bernardon et al.

[11] Patent Number: 5,877,342
[45] Date of Patent: Mar. 2, 1999

[54] ADAMANTYL-SUBSTITUTED BIAROMATIC COMPOUNDS AND PHARMACEUTICAL/COSMETIC COMPOSITIONS COMPRISED THEREOF

[75] Inventors: Jean-Michel Bernardon, Le Rouret; Bruno Charpentier, Biot, both of France

[73] Assignee: Centre International De Recherches Dermatologiquies Galderma, Valbonne, France

[21] Appl. No.: 757,638

[22] Filed: Dec. 2, 1996

[30] Foreign Application Priority Data

Dec. 1, 1995 [FR] France ................................. 95 14261

[51] Int. Cl.$^6$ .................................................. C07C 69/76
[52] U.S. Cl. ......................... 560/102; 562/492; 514/532; 514/569
[58] Field of Search ........................... 560/102; 562/492; 514/532, 569

[56] References Cited

FOREIGN PATENT DOCUMENTS 0514264  11/1992  European Pat. Off. .

OTHER PUBLICATIONS

Congr. Int. Technol. Pharm., 5th, No. 3, 1989, pp. 375–383.

*Primary Examiner*—Paul J. Killos
*Attorney, Agent, or Firm*—Burns, Doane, Swecker & Mathis, L.L.P.

[57] ABSTRACT

Novel pharmaceutically/cosmetically-active adamantyl-substituted biaromatic compounds have the structural formula (I):

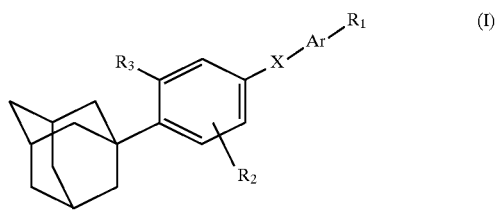

wherein Ar is a radical having one of the formulae (a')–(f'):

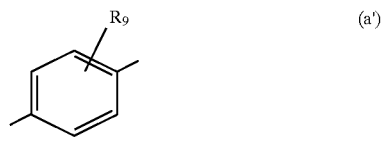

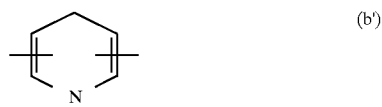

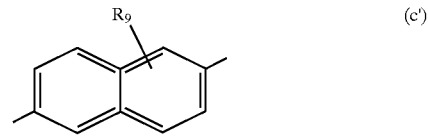

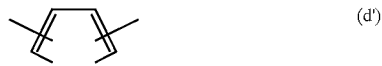

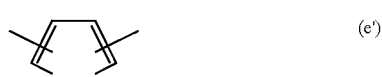

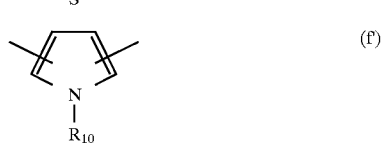

and are useful for the treatment of a wide variety of disease states, whether human or veterinary, for example dermatological, rheumatic, respiratory, cardiovascular, bone and ophthalmological disorders, as well as for the treatment of mammalian skin and hair conditions/disorders.

58 Claims, 4 Drawing Sheets

ADAMANTYL-SUBSTITUTED BIAROMATIC COMPOUNDS AND PHARMACEUTICAL/COSMETIC COMPOSITIONS COMPRISED THEREOF

CROSS-REFERENCE TO COMPANION APPLICATIONS

Copending applications Ser. No. _____ [Attorney Docket No. 016800-130], filed concurrently herewith, and Ser. No. 08/429,045, filed Apr. 26, 1995 and now U. S. Pat. No. 5,574,036; each is assigned to the assignee hereof.

BACKGROUND OF THE INVENTION

Technical Field of the Invention

The present invention relates to novel adamantyl-substituted biaromatic compounds and to pharmaceutical/cosmetic compositions comprised thereof; the subject compounds are especially useful in human or veterinary medicine, or, alternatively, in cosmetic compositions.

SUMMARY OF THE INVENTION

The compounds according to the invention display marked activity in the fields of cell differentiation and proliferation and are particularly useful in the topical and systemic treatment of dermatological conditions/afflictions associated with a keratinization disorder, dermatological (or other) conditions/afflictions including an inflammatory and/or immunoallergic component, and dermal or epidermal proliferations, whether benign or malignant. The subject compounds can, in addition, be used for the treatment of diseases of connective tissue degeneration, to combat aging of the skin, whether photoinduced or chronological, and to treat cicatrization or healing disorders. Moreover, they are also useful for ophthalmological applications, especially for the treatment of corneopathies.

The compounds according to the invention can also be formulated into cosmetic compositions for body and hair care/hygiene.

Briefly, the adamantyl-substituted biaromatic compounds according to this invention have the following structural formula (I):

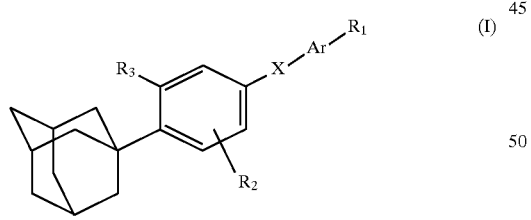

in which $R_1$ is a —$CH_3$ radical, a —$(CH_2)n$—O—$R_4$ radical, an —O—$(CH_2)m$—$(CO)n$—$R_5$ radical, a —CO—$R_6$ radical, or a —CO—O—$R_7$ radical, wherein the values of m and n and the radicals $R_4$ to $R_7$ are as defined below; $R_2$ is a hydrogen atom, a halogen atom, a linear or branched alkyl radical having from 1 to 20 carbon atoms, an —$OR_4$ radical, or an —O—$CH_2$—O—$CH_2$—$CH_2$—O—$CH_3$ radical; $R_3$ is a —Y—$(CH_2)p$—Y—$(CH_2)q$—$R_8$ radical, a —$(CH_2)p$—$(Y)_s$—$(CH_2)q$—$R_8$ radical, a —Y—$(CH_2)q$—$R_8$ radical, or a —CH=CH—$(CH_2)r$—$R_8$ radical, wherein the values of p, q, r and s and the radicals Y and $R_8$ are as defined below; X is a bridging radical selected from among the following formulae (a)–(m), which may be left-to-right or right-to-left:

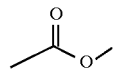 (a)

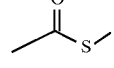 (b)

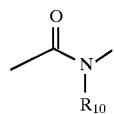 (c)

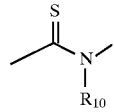 (d)

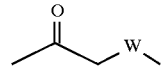 (e)

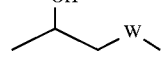 (f)

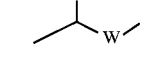 (g)

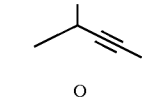 (h)

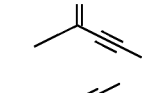 (i)

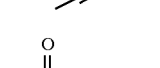 (j)

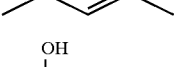 (k)

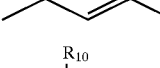 (l)

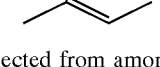 (m)

Ar is a radical selected from among those of the following formulae (a')–(f'):

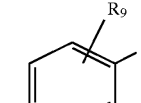 (a')

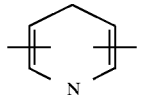 (b')

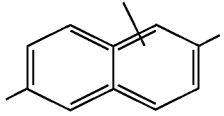 (c')

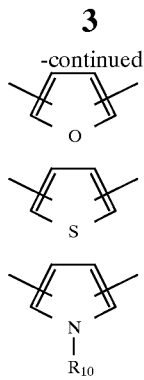

m is an integer equal to 1, 2 or 3; n is an integer equal to 0 or 1; p is an integer ranging from 1 to 12, inclusive; q is an integer ranging from 0 to 12, inclusive; r is an integer ranging from 0 to 10, inclusive; s is an integer equal to 0 and 1; t is an integer equal to 0, 1 or 2; Y is an oxygen atom or a radical S(O)t; W is an oxygen atom, a radical S(O)t or a radical N—$R_{10}$; $R_4$ is a hydrogen atom, a lower alkyl radical or a radical —CO—$R_{11}$; $R_5$ is a lower alkyl radical or a heterocycle; $R_6$ is a hydrogen atom, a lower alkyl radical, or a radical:

in which R' and R", which may be identical or different, are each a hydrogen atom, a lower alkyl radical, a mono- or polyhydroxyalkyl radical, an optionally substituted aryl radical, or an amino acid or peptide or sugar residue, with the proviso that R' and R" may together form, with the nitrogen atom from which they depend, a nitrogen-containing heterocycle; $R_7$ is a hydrogen atom, a linear or branched alkyl radical having from 1 to 20 carbon atoms, an alkenyl radical, a mono- or polyhydroxyalkyl radical, an optionally substituted aryl or aralkyl radical, or a sugar residue or an amino acid or peptide residue; $R_8$ is a hydrogen atom, a branched alkyl radical having from 1 to 20 carbon atoms, a C3–C6 cycloaliphatic radical, a monohydroxyalkyl radical or a polyhydroxyalkyl radical, said hydroxyls optionally being protected as methoxy, acetoxy or acetonide groups, an aryl radical, an alkenyl radical, an alkynyl radical, a —CO—$R_6$ radical, a —CO—O—$R_7$ radical, an amino alkyl radical whose amine function is optionally substituted with one or two lower alkyl radicals, or a heterocycle, wherein $R_7$ is as defined above; $R_9$ is a hydrogen or halogen atom, a linear or branched alkyl radical having from 1 to 20 carbon atoms, an —O$R_4$ radical or an —O—$CH_2$—O—$CH_2$—$CH_2$—O—$CH_3$ radical; the radicals $R_{10}$, which may be identical or different, are each a hydrogen atom or a lower alkyl radical; and $R_{11}$ is a lower alkyl radical, with the proviso that, when X is a bridging radical of formula (e) and $R_3$ is a radical —Y—$(CH_2)_q$—$R_8$ wherein Y is an oxygen atom and $R_8$ is a hydrogen atom, then q must be greater than 6.

This invention also features the salts of the compounds of formula (I) in the event that $R_1$ or $R_8$ represents a carboxylic acid function and/or when $R_8$ represents an amine function, the chiral (optical) analog and the geometrical isomers thereof. When the compounds according to the invention exist in the form of salts, by addition of an acid, they are pharmaceutically or cosmetically acceptable salts obtained by addition of an inorganic or organic acid thereto, in particular hydrochloric acid, sulfuric acid, acetic acid, citric acid, fumaric acid, hemisuccinic acid, maleic acid and mandelic acid. When the compounds according to the invention are in the form of salts by addition of a base, they are preferably salts of an alkali metal or alkaline earth metal or, alternatively, of zinc or of an organic amine.

Figure 1:
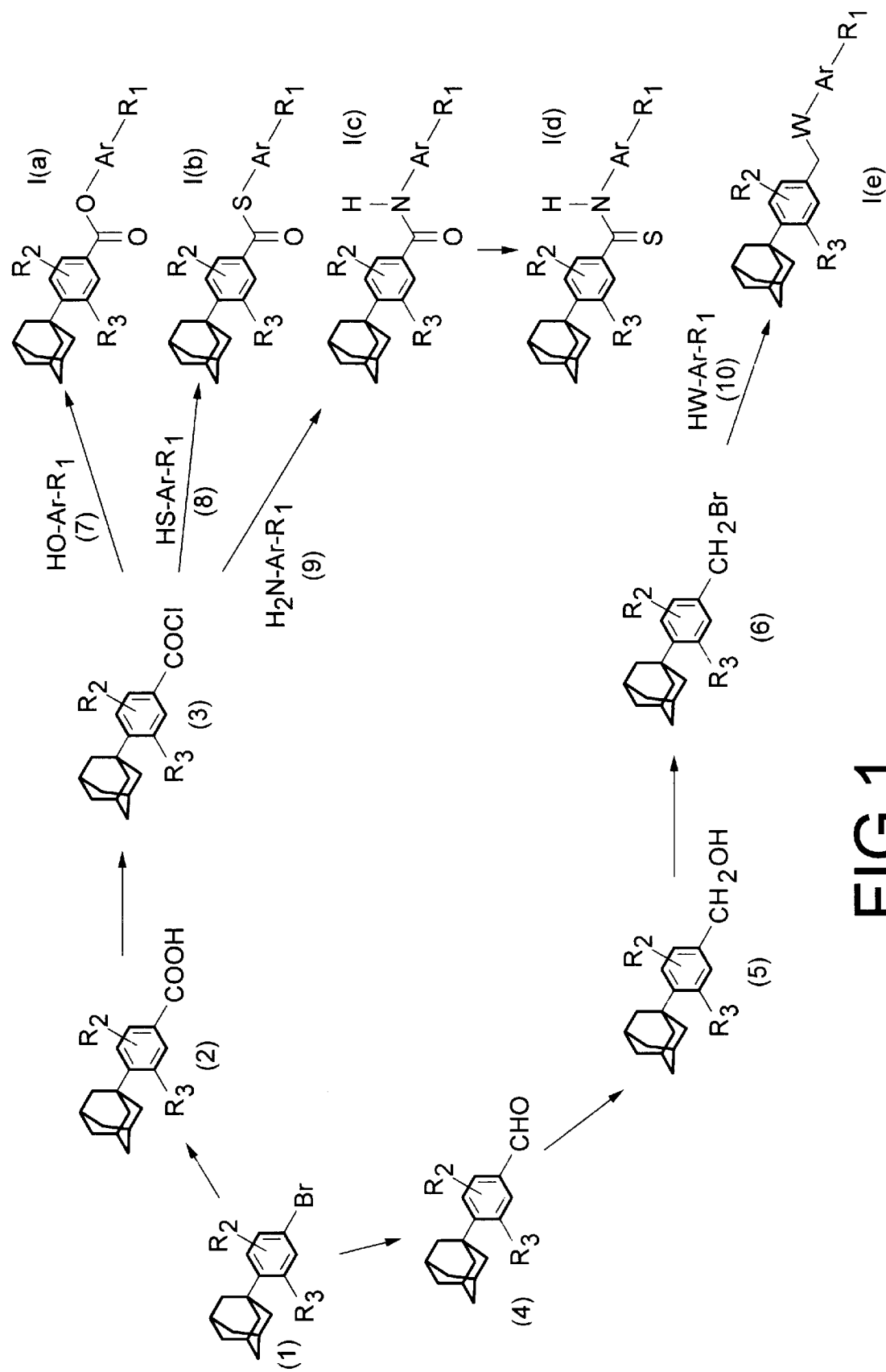
FIGS. 1, 2, 3 and 4 set forth reaction schemes/mechanisms illustrating representative syntheses for the preparation of the adamantyl-substituted biaromatic compounds according to the present invention.

DETAILED DESCRIPTION OF BEST MODE AND SPECIFIC/PREFERRED EMBODIMENTS OF THE INVENTION

More particularly, according to the present invention, by the term "lower alkyl radical" is intended an alkyl radical having from 1 to 12, preferably from 1 to 9, carbon atoms, advantageously the methyl, ethyl, isopropyl, butyl, tert-butyl, hexyl, nonyl and dodecyl radicals.

By the term "linear alkyl radical having from 1 to 20 carbon atoms" is preferably intended the methyl, ethyl, propyl, 2-ethylhexyl, octyl, dodecyl, hexadecyl and octadecyl radicals.

By the term "branched alkyl radical having from 1 to 20 carbon atoms" is preferably intended the 2-methylbutyl, 2-methylpentyl, 1-methylhexyl and 3-methylheptyl radicals.

By "monohydroxyalkyl radical" is intended a radical preferably having 2 or 3 carbon atoms, especially a 2-hydroxyethyl, 2-hydroxypropyl or 3-hydroxypropyl radical.

By "polyhydroxyalkyl radical" is intended a radical preferably having from 3 to 6 carbon atoms and from 2 to 5 hydroxyl groups, such as the 2,3-dihydroxypropyl, 2,3,4-trihydroxybutyl and 2,3,4,5-tetrahydroxypentyl radicals, or the pentaerythritol residue.

By "aryl radical" is preferably intended a phenyl radical optionally substituted by at least one halogen atom, or at least one hydroxyl or nitro functional group.

By "aralkyl radical" is preferably intended the benzyl or phenethyl radical optionally substituted by at least one halogen atom, or at least one hydroxyl or nitro functional group.

By "alkenyl radical" is intended a radical preferably having from 2 to 5 carbon atoms and one or more sites of ethylenic unsaturation, such as, more particularly, the allyl radical.

By the term "sugar residue" is intended a residue derived especially from glucose, from galactose or from mannose, or, alternatively, from glucuronic acid.

By the term "amino acid residue" is especially intended a residue derived from lysine, from glycine or from aspartic acid, and by the term "peptide residue" is more particularly intended a dipeptide or tripeptide residue prepared via the combination of amino acids.

By the term "heterocycle" is preferably intended a piperidino, morpholino, pyrrolidino or piperazino radical, optionally substituted in the 4-position by a $C_1$–$C_6$ alkyl or mono- or polyhydroxyalkyl radical as defined above.

By the term "amino alkyl radical" is preferably intended a radical having from 1 to 6 carbon atoms, in particular the aminomethyl, 3-aminopropyl and 6-aminohexyl radicals.

By "alkynyl radical" is preferably intended a radical having from 2 to 6 carbon atoms, in particular a propargyl radical.

And by "cycloaliphatic radical" is preferably intended a radical having from 3 to 6 carbon atoms, in particular the cyclopropyl and cyclohexyl radicals.

When the radicals $R_2$ and $R_9$ are halogen atoms, they are preferably a fluorine, bromine or chlorine atoms.

Among the compounds of formula (I) according to the present invention, particularly representative are the following:

4-[4-(1-Adamantyl)-3-methoxybenzoyloxy]benzoic acid;

(E)-4-[[2-[4-(1-Adamantyl)-3-hydroxyphenyl]ethenyl]] benzoic acid;

(E)-4-[[2-[4-(1-Adamantyl)-3-propyloxyphenyl]ethenyl]] benzoic acid;

(E)-4-[[2-[4-(1-Adamantyl)-3-heptyloxyphenyl]ethenyl]] benzoic acid;

(E)-4-[[2-[4-(1-Adamantyl)-3-methoxyphenyl]ethenyl]] benzoic acid;

4-[4-(1-Adamantyl)-3-methoxyethoxymethoxyphenylethynyl]benzoic acid;

(E)-4-[[2-[4-(1-Adamantyl)-3-(5-carbamoylpentyloxy) phenyl]ethenyl]]benzoic acid;

(E)-4-[[2-[4-(1-Adamantyl)-3-methoxyphenyl]-1-propenyl]]benzoic acid;

(E)-4-[[2-[4-(1-Adamantyl)-3-(3-hydroxypropyloxy) phenyl]ethenyl]]benzoic acid;

(E)-4-[[2-[4-(1-Adamantyl)-3-(6-hydroxyhexyloxy) phenyl]ethenyl]]benzoic acid;

4-[[3-oxo-3-[4-(1-Adamantyl)-3-methoxyphenyl]-1-propenyl]]benzoic acid;

4-[4-(1-Adamantyl)-3-methoxyethoxymethoxybenzoylthio]benzoic acid;

4-[4-(1-Adamantyl)-3-methoxyethoxymethoxybenzoyloxy]benzoic acid;

4-[4-(1-Adamantyl)-3-methoxyethoxymethoxybenzamido]benzoic acid;

(E)-4-[2-(4-(1-Adamantyl)-3-methoxyethoxymethoxyphenyl)ethenyl]benzoic acid;

(E)-4-[2-(4-(1-Adamantyl)-3-methoxyethoxymethoxyphenyl)-1-propenyl]benzoic acid;

(Z)-4-[2-(4-(1-Adamantyl)-3-methoxyethoxymethoxyphenyl)-1-propenyl]benzoic acid;

4-[4-(1-Adamantyl)-3-methoxyethoxymethoxybenzoylmethyloxy]benzoic acid;

4-[[3-Oxo-3-[4-(1-adamantyl)-3-methoxyethoxymethoxyphenyl]-1-propynyl]]benzoic acid;

4-[[3-Hydroxy-3-[4-(1-adamantyl)-3-methoxyethoxymethoxyphenyl]-1-propynyl]]benzoic acid;

(E)-4-[[3-Oxo-3-[4-(1-adamantyl)-3-methoxyethoxymethoxyphenyl]-1-propenyl]]benzoic acid;

4-[[3-Hydroxy-3-[4-(1-adamantyl)-3-methoxyethoxymethoxyphenyl]-1-propenyl]]benzoic acid;

Allyl 4-[4-(1-adamantyl)-3-methoxyethoxymethoxythiobenzamido]benzoate;

4-[[3-Hydroxy-3-[4-(1-adamantyl)-3-methoxyphenyl]-1-propynyl]]benzoic acid;

2-Hydroxy-4-[[3-hydroxy-3-[4-(1-adamantyl)-3-methoxyphenyl]-1-propynyl]]benzoic acid;

2-Hydroxy-4-[[3-hydroxy-3-[4-(1-adamantyl)-3-methoxyethoxymethoxyphenyl]-1-propynyl]]benzoic acid;

4-[[3-Hydroxy-3-[4-(1-adamantyl)-3-methoxyethoxymethoxyphenyl]-1-propynyl]]benzaldehyde;

4-[[3-Hydroxy-3-[4-(1-adamantyl)-3-methoxyethoxymethoxyphenyl]-1-propynyl]]benzenemethanol;

N-Ethyl-4-[4-(1-adamantyl)-3-methoxyethoxymethoxyphenylethynyl]benzamide;

N-(4-Hydroxyphenyl)-4-[4-(1-adamantyl)-3-methoxyethoxymethoxyphenylethynyl]benzamide;

4-[4-(1-Adamantyl)-3-methoxyethoxymethoxyphenylethynyl]phenol;

According to the present invention, the compounds of formula (I) which are the more particularly preferred are those in which at least one, and preferably all, of the following conditions is satisfied:

$R_1$ is the radical —COO—$R_7$ or —CO—$R_6$;

$R_3$ is the radical —Y—$(CH_2)p$—Y—$(CH_2)q$—$R_8$, —$(CH_2)p$—(Y)n—$(CH_2)q$—$R_8$ or —Y—$(CH_2)q$—$R_8$;

X is a bridging radical of formula (a), (h), (i), (j), (k) or (m); and

Ar is a radical of formula (a') or (b').

The present invention also features processes for the preparation of the compounds of formula (I), in particular via the reaction schemes illustrated in FIGS. 1, 2, 3 and 4.

Thus, the compounds of formula I(a) can be prepared (FIG. 1) by reacting in anhydrous medium, in an organic solvent, preferably THF, and in the presence of a tertiary amine (for example triethylamine or pyridine), an activated form of a benzoic acid (2), for example an acid chloride (3), with a phenolic compound of formula (7).

The compounds of formula I(b) can be prepared (FIG. 1) by reacting in anhydrous medium, in an organic solvent, preferably THF, and in the presence of a tertiary amine (for example triethylamine or pyridine), an activated form of a benzoic acid (2), for example an acid chloride (3), with a thiophenolic compound of formula (8).

The compounds of formula I(c) can be prepared (FIG. 1) by reacting in anhydrous medium, in an organic solvent, preferably THF, and in the presence of a tertiary amine (for example triethylamine or pyridine), an activated form of an aromatic carboxylic acid (2), for example an acid chloride (3), with an amino compound of formula (9).

The compounds of formula I(d) can be prepared (FIG. 1) from compounds of formula 1(c) via reaction with Lawesson's reagent.

The compounds of formula 1(e) can be prepared (FIG. 1) from benzyl alcohols (5) via conversion of same into bromo derivatives (6) with phosphorus tribromide and then reaction in the presence of potassium carbonate or an alkali metal hydride (sodium hydride), or by phase transfer using, for example, tetrabutylammonium bromide as quaternary salt, with a compound (10) bearing a hydroxyl or thiol or amino functional group.

The compounds of formula I(f) can be prepared (FIG. 2) from acetophenone derivatives (11) via conversion of same into bromo derivative (12) using bromine and then reaction in the presence of potassium carbonate or an alkali metal hydride (sodium hydride), or by phase transfer using, for example, tetrabutylammonium bromide as quaternary salt, with a compound (10) bearing a hydroxyl or thiol or amino functional group.

The compounds of formula I(g) can be prepared from the derivative I(f) by reacting same with sodium borohydride in an alcoholic solvent.

Thus, the compounds of formula I(h) can be prepared (FIG. 2) from acetophenone derivatives (11) by reacting same with aromatic aldehyde derivatives (13) in the presence of sodium methoxide or sodium hydroxide in an alcoholic solvent such as methanol. By reacting these compounds with sodium borohydride in the presence of cerium trichloride, the compounds of formula I(i) are prepared.

And the compounds of formula I(j) can be prepared (FIG. 2) from aromatic aldehyde derivatives (4) by reacting same with lithium trimethylsilylacetylenide and then deprotection or unblocking with tetrabutylammonium fluoride to obtain the α-hydroxyacetylenic derivatives (14). This is followed by coupling with the halo derivatives (15), preferably iodo derivatives, in the presence of a palladium catalyst (for example bis(triphenylphosphine)palladium(II) chloride, in a solvent such as triethylamine. The oxidation of these compounds with either pyridinium dichromate or manganese oxide or the Swern reagent provides the derivatives of formula I(k).

The compounds of formula I(m) can be prepared (FIG. 3) from the aromatic aldehyde derivatives (4) by reacting same with carbon teterabromide and triphenylphosphine to give 2', 2'-dibromostyrene derivatives (16) which are then converted into acetylenic derivatives (17) by the action of n-butyllithium in a solvent such as THF. This is followed by coupling with the halo derivatives (15), preferably the iodo derivatives, in the presence of a palladium catalyst, for example bis(triphenylphosphine)palladium(II) chloride, in a solvent such as triethylamine.

The compounds of formulae I(p) and I(n) can be prepared (FIG. 3) from the aromatic aldehyde derivatives (4) and from the acetophenone derivatives (11), respectively, according to a reaction of Horner-Emmons or Wittig type with aromatic phosphonate derivatives (18) or aromatic phosphine derivatives.

When $R_3$ is a radical —$(CH_2)p$—$(Y)_n$—$(CH_2)q$—$R_8$ or —CH=CH—$(CH_2)r$—$R_8$, the compounds can be prepared (FIG. 4 in which s is equal to p2) from phenolic derivatives (19) which are converted into triflate derivatives (20), followed by nucleophilic substitution in the presence of a palladium catalyst, according to the general conditions described in S. Cacchi et al, *Tetrahedron Letters*, 27, 3931–3934 (1986), W. J. Scott et al, *J. Org. Chem.*, 50, 2302–2308 (1985), and J. K. Stille et al, *J. Am. Chem. Soc.*, 109, 5478–5486 (1987).

When $R_1$ is the —COOH radical, the compounds are prepared by protecting $R_1$ with a protecting group of alkyl, allyl, benzyl or tert-butyl type.

Conversion into the free form may be carried out:
 (i) in the case of an alkyl protecting group, using sodium hydroxide or lithium hydroxide in an alcoholic solvent such as methanol or in THF;
 (ii) in the case of an allylic protecting group, using a catalyst such as certain transition metal complexes in the presence of a secondary amine such as morpholine;
 (iii) in the case of a benzylic protecting group, by debenzylation in the presence of hydrogen using a catalyst such as palladium-on-charcoal;
 (iv) in the case of a protecting group of tert-butyl type, using trimethylsilyl iodide.

The present invention also features therapeutic/pharmaceutical applications of the compounds of formula (I).

These compounds exhibit activity in the test of differentiation of mouse embryonic teratocarcinoma cells (F9) (*Cancer Research*, 43, p. 5268 (1983)) and/or in the test of inhibition of ornithine decarboxylase after induction with TPA in mice (*Cancer Research*, 38, p. 793–801 (1978)). These tests demonstrate the activities of these compounds in the fields of cell differentiation and proliferation, respectively. In the test of differentiation of the cells (F9), it is possible to evaluate an agonist activity as an antagonist activity towards retinoic acid receptors. An antagonist is inactive when it is alone in this test, but partially or totally inhibits the effect elicited by an agonist retinoid on the morphology and on the secretion of the plasminogen activator. Certain of these compounds therefore also exhibit an activity in a test which entails identifying RAR-antagonist molecules, as described in French patent application No. 95/07302, filed Jun. 19, 1995 and assigned to the assignee hereof. This test comprises the following steps: (i) a sufficient amount of an RAR-agonist molecule is applied topically to an area of the skin of a mammal, (ii) a molecule capable of exhibiting an RAR-antagonist activity is administered systemically or topically to this same mammal or to this same area of the mammal's skin, before, during or after step (i), and (iii) the response by the mammal's skin thus treated is evaluated. Thus, the response to a topical application of an RAR-agonist molecule to the ear of a mammal, which corresponds to an increase in the thickness of this ear, may be inhibited by the systemic or topical administration of an RAR-antagonist molecule.

The compounds according to the invention are particularly well suited in the following fields of therapy:
 (1) for treating dermatological conditions/afflictions associated with a keratinization disorder related to differentiation and proliferation, in particular for treating simple acne, comedones, polymorphonuclear leukocytes, rosacea, nodulocystic acne, acne conglobata, senile acne and secondary acnes such as solar, medication-related or occupational acne,
 (2) for treating other types of keratinization disorders, in particular ichthyosis, ichthyosiform states, Darier's disease, palmoplantar keratoderma, leukoplasias and leukoplasiform states, and cutaneous or mucosal (oral) lichen,
 (3) for treating other dermatological conditions/afflictions associated with a keratinization disorder manifesting an inflammatory and/or immunoallergic component and, in particular, all forms of psoriasis, whether cutaneous, mucosal or ungual psoriasis, and even psoriatic rheumatism, or alternatively cutaneous atopy, such as eczema or respiratory atopy or, alternatively, gingival hypertrophy; the compounds may also be used in certain inflammatory conditions which do not display any keratinization disorder,
 (4) for treating all dermal or epidermal proliferations, whether benign or malignant and whether or not of viral origin, such as common warts, flat warts and verruciform epidermodysplasia, and the oral or florid papillomatoses and the proliferations induced by ultraviolet radiation, in particular in the case of basocellular and spinocellular epithelioma,
 (5) for treating other dermatological disorders such as bullosis and collagen diseases,
 (6) for treating certain ophthalmological disorders, especially corneopathies,
 (7) for repairing or combating aging of the skin, whether photoinduced or chronological aging, or for reducing actinic keratoses and pigmentations, or any pathologies associated with chronological or actinic aging, (8) for preventing or curing the stigmata of epidermal and/or dermal atrophy induced by local or systemic corticosteroids, or any other form of cutaneous atrophy, (9) for preventing or treating cicatrization or healing disorders, or for preventing or repairing vibices (stretch marks),

(10) for combating disorders of sebaceous functioning, such as the hyperseborrhoea of acne or simple seborrhoea,

(11) for the treatment or prevention of cancerous or precancerous states,

(12) for the treatment of inflammatory conditions such as arthritis,

(13) for the treatment of any skin or general condition/affliction of viral origin,

(14) for the prevention or treatment of alopecia,

(15) for the treatment of dermatological or general conditions/afflictions including an immunological component,

(16) for the treatment of conditions/afflictions of the cardiovascular system such as arteriosclerosis, For the aforesaid therapeutic or pharmaceutical applications, the compounds according to the invention may advantageously be employed in combination with other compounds exhibiting retinoid-type activity, with the D vitamins or derivatives thereof, with corticosteroids, with anti-free-radical agents, with α-hydroxy or α-keto acids or derivatives thereof, or, alternatively, with ion-channel blockers. By the term "D vitamins or derivatives thereof" are intended, for example, derivatives of vitamin $D_2$ or $D_3$ and in particular 1,25-dihydroxyvitamin $D_3$. By the term "anti-free-radical agents" are intended, for example, α-tocopherol, superoxide dismutase, ubiquinol or certain metal-chelating agents. By the term "α-hydroxy or α-keto acids or derivatives thereof" are intended, for example, lactic acid, malic acid, citric acid, glycolic acid, mandelic acid, tartaric acid, glyceric acid or ascorbic acid or the salts, amides or esters thereof. Lastly, by the term "ion-channel blockers" are intended, for example, minoxidil (2,4-diamino-6-piperidinopyrimidine 3-oxide) and derivatives thereof.

The present invention thus also features medicinal compositions containing at least one compound of formula (I), one of the optical or geometrical isomers thereof, or one of the pharmaceutically accepetable salts, or other derivatives thereof.

The pharmaceutical/therapeutic compositions of the present invention, intended especially for the treatment of the aforesaid disease states comprise a pharmaceutically acceptable vehicle, carrier or diluent which is compatible with the mode or regimen of administration selected for the given composition, at least one compound of formula (I), one of the optical or geometrical isomers thereof, or one of the salts, etc., thereof.

The compounds according to the invention may be administered via the systemic, enteral, parenteral, topical or ocular route.

For enteral administration, the medicinal/pharmaceutical compositions may be in the form of tablets, gelatin capsules, dragees, syrups, suspensions, solutions, elixirs, powders, granules, emulsions, microspheres or nanospheres or lipidic or polymeric vesicles which permit a controlled release. For parenteral administration, the compositions may be in the form of solutions or suspensions for infusion or for injection.

The compounds according to the invention are generally administered at a daily dose of approximately 0.01 mg/kg to 100 mg/kg of body weight, and this at the rate or regime of 1 to 3 doses per diem.

For topical administration, the pharmaceutical compositions based on compounds according to the invention are more particularly intended for the treatment of the skin and the mucosae and may then be in the form of pasty ointments, creams, milks, salves, creamy ointments, powders, impregnated pads, solutions, gels, sprays, lotions or suspensions. They may also be in the form of microspheres or nanospheres or lipidic or polymeric vesicles or polymeric patches and hydrogels which permit a controlled release. These topical-route compositions may, moreover, be either in anhydrous form or in an aqueous form, depending on the particular clinical indication.

For ocular administration, they are principally eye drops.

These compositions for topical or ocular application contain at least one compound of formula (I), or one of the optical or geometrical isomers thereof or, alternatively, one of the salts, etc., thereof, at a concentration preferably ranging from 0.001% to 5% by weight relative to the total weight of the composition.

The compounds of formula (I) according to the invention also find application in the cosmetics field, in particular body and hair care/hygiene, and especially for treating skin-types with a tendency towards acne, for promoting the regrowth of the hair, for combating hair loss, for controlling the greasy appearance of the skin or of the hair, for protection against the harmful aspects of the sun or for the treatment of physiologically dry skin-types, and for preventing and/or combating photoinduced or chronological aging.

For cosmetic applications, the compounds according to the invention may, moreover, advantageously be employed in combination with other compounds having retinoid-type activity, with the D vitamins or derivatives thereof, with corticosteroids, with anti-free-radical agents, with α-hydroxy or α-keto acids or derivatives thereof, or, alternatively, with ion-channel blockers, all of these various active agents being as defined above.

The present invention thus also features cosmetic compositions comprising a cosmetically acceptable vehicle suitable for topical application, at least one compound of formula (I), or one of the optical or geometrical isomers thereof, or one of the salts, etc., thereof. Such cosmetic compositions are advantageously in the form of a cream, a milk, a lotion, an ointment, a gel, lipidic or polymeric microspheres or nanospheres or vesicles, a soap or a shampoo.

The concentration of the compound of formula (I) in the cosmetic compositions according to the invention advantageously ranges from 0.001% to 3% by weight relative to the total weight of the composition.

The medicinal and cosmetic compositions according to the invention may additionally contain inert additives and adjuvants, or even pharmacodynamically or cosmetically active additives and adjuvants, or combinations thereof, and especially: wetting agents; depigmenting agents such as hydroquinone, azelaic acid, caffeic acid or kojic acid; emollients; hydrating agents such as glycerol, PEG 400, thiamorpholine and derivatives thereof or alternatively urea; anti-seborrhoeic agents or anti-acne agents such as S-carboxymethylcysteine and S-benzylcysteamine and the salts or derivatives thereof, or benzoyl peroxide; antibiotics such as erythromycin and the esters thereof, neomycin, clindamycin and the esters thereof, and tetracyclines; antifungal agents such as ketoconazole or poly-4,5-methylene- 3-isothiazolidones; agents promoting the regrowth of the hair, such as minoxidil (2,4-diamino-6-piperidinopyrimidine 3-oxide) and derivatives thereof, diazoxide (7-chloro-3-methyl-1,2,4-benzothiadiazine 1,1-dioxide) and phenytoin (5,5-diphenylimidazolidine-2,4-dione); non-steroidal anti-inflammatory agents; carotenoids and in particular β-carotene; anti-psoriatic agents such as anthraline and derivatives thereof; and, lastly, eicosa-5,8,11,14-tetraynoic acid and eicosa-5,8,11-triynoic acid, and the esters and amides thereof.

The compositions according to the invention may also contain flavor-enhancing agents, preservatives such as para-hydroxybenzoic acid esters, stabilizers, moisture regulators, pH regulators, osmotic pressure modifiers, emulsifying agents, UV-A and UV-B screening agents, and antioxidants such as α-tocopherol, butylhydroxyanisole or butylhydroxytoluene.

In order to further illustrate the present invention and the advantages thereof, the following specific examples are given, it being understood that same are intended only as illustrative and in nowise limitative.

EXAMPLE 1

Preparation of 4-[4-(1-adamantyl)-3-methoxybenzoyloxy]benzoic acid (a) Preparation of 2-(1-adamantyl)-5-bromophenol:

17 g (0.1 mol) of 3-bromophenol, 15.2 g (0.1 mol) of 1-adamantanol and 50 ml of dichloromethane were introduced into a round-bottomed flask. 5 ml of concentrated sulfuric acid were added dropwise and the mixture was stirred at room temperature for 24 hours. The reaction medium was poured into icewater, neutralized with sodium bicarbonate and extracted with ethyl ether. The organic phase was separated out after settling had taken place, dried over magnesium sulfate and evaporated. The residue obtained was purified by chromatography on a column of silica, eluted with a mixture of dichloromethane and hexane (50/50). 15.2 g (50%) of the expected phenol, having a melting point of 112°–4° C., were recovered.

(b) Preparation of 4-(1-adamantyl)-1-bromo-3-methoxybenzene:

1.6 g (53 mmol) of sodium hydride (80% in oil) and 50 ml of DMF were introduced into a three-necked flask. A solution of 15 g (49 mmol) of 2-(1-adamantyl)-5-bromophenol in 100 ml of DMF was added dropwise and the mixture was stirred until the evolution of gas had ceased. 3 ml (49 mmol) of methyl iodide were then added, while cooling in a bath of ice, and the mixture was stirred at room temperature for 6 hours. The reaction medium was poured into water and extracted with ethyl ether. The organic phase was separated out after settling had taken place, dried over magnesium sulfate and evaporated. The residue obtained was triturated from hexane, filtered and dried. 12.6 g (80%) of the expected compound, having a melting point of 155°–60° C., were recovered.

(c) Preparation of 4-(1-adamantyl)-3-methoxybenzoic acid:

The above compound (b) (11.3 g, 35 mmol) was dissolved in 200 ml of THF. The solution obtained was added dropwise to magnesium (1.3 g, 52.5 mmol) and a crystal of iodine. After introduction, the mixture was heated at reflux for two hours, cooled to −78° C. and a stream of CO$_2$ was passed therethrough for one hour. The reaction medium was permitted to warm to room temperature, poured into saturated aqueous ammonium chloride solution and extracted with ethyl ether. The organic phase was separated out after settling had taken place, dried over magnesium sulfate and evaporated. The residue obtained was purified by chromatography on a column of silica, eluted with a mixture of dichloromethane and ethyl ether (90/10). 5.1 g (51%) of the expected acid, having a melting point of 259°–60° C., were recovered.

(d) Preparation of 4-(1-adamantyl)-3-methoxybenzoyl chloride:

2.1 g (7.34 mmol) of 4-(1-adamantyl)-3-methoxybenzoic acid and 20 ml of thionyl chloride were introduced into a round-bottomed flask and the mixture was heated at reflux until the evolution of gas had ceased. The reaction medium was evaporated to dryness and 2.2 g (100%) of the acid chloride, which was used without further purification in the remainder of the synthesis, were recovered.

(e) Preparation of benzyl 4-[4-(1-adamantyl)-3-methoxybenzoyloxy]benzoate:

1.67 g (7.34 mmol) of benzyl 4-hydroxybenzoate, 1 ml (7.34 mmol) of triethylamine and 40 ml of THF were introduced into a round-bottomed flask. A solution of 2.2 g (7.34 mmol) of 4-(1-adamantyl)-3-methoxybenzoyl chloride was added dropwise and the mixture was stirred at room temperature for 8 hours. The reaction medium was poured into water and extracted with ethyl ether. The organic phase was separated out after settling had taken place, dried over magnesium sulfate and evaporated. The residue obtained was purified by chromatography on a column of silica, eluted with a mixture of dichloromethane and hexane (60-40). After evaporation of the solvents, 3.1 g (85%) of the expected benzyl ester, having a melting point of 128°–9° C., were recovered.

(f) Synthesis of 4-[4-(1-adamantyl)-3-methoxybenzoyloxy]benzoic acid:

1.8 g (3.6 mmol) of benzyl 4-[4-(1-adamantyl)-3-methoxybenzoyloxy]benzoate and 50 ml of dioxane were introduced into a reactor. After flushing the reactor with nitrogen, 1 g of Pd-on-charcoal (10%) was introduced, followed by hydrogen at a pressure of 7.5 bar. The mixture was stirred at room temperature for 3 hours, the catalyst was filtered off and the filtrate was evaporated. The residue obtained was triturated from 40 ml of ethyl ether and filtered. 1.1 g (71%) of the expected acid, having a melting point of 273°–4° C., was recovered.

EXAMPLE 2

Preparation of (E)-4-[[2-[4-(1-adamantyl)-3-hydroxyphenyl]ethenyl]]benzoic acid (a) Preparation of 4-(1-adamantyl)-1-bromo-3-tert-butyldimethylsilyloxybenzene:

15.36 g (50 mmol) of 2-(1-adamantyl)-5-bromophenol, 150 ml of DMF, 7.7 ml (55 mmol) of triethylamine and 305 mg of 4-dimethylaminopyridine were successively introduced into a round-bottomed flask and a solution of 8.3 g (55 mmol) of tert-butyldimethylsilyl chloride was added and the mixture was stirred at room temperature for 12 hours. The reaction medium was poured into water and extracted with ethyl ether. The organic phase was separated out after settling had taken place, dried over magnesium sulfate and evaporated. The solid obtained was recrystallized from acetone and 19.9 g (94%) of the expected compound, having a melting point of 86°–8° C., were recovered.

(b) Preparation of 4-(1-adamantyl)-3-tert-butyldimethylsilyloxybenzenecarboxaldehyde:

In a manner analogous to that of to Example 6(a), from 19.8 g (47 mmol) of 4-(1-adamantyl)-1-bromo-3-tert-butyldimethylsilyloxybenzene, 14.8 g (85%) of the expected aldehyde, having a melting point of 114°–6° C., were recovered.

(c) Preparation of ethyl (E)-4-[[2-[4-(1-adamantyl)-3-hydroxyphenyl]ethenyl]]benzoate:

724 mg (24 mmol) of sodium hydride (80% in oil) and 50 ml of THF were introduced into a three-necked flask under a stream of nitrogen. A solution of 7.4 g (20 mmol) of 4-(1-adamantyl)-3-tert-butyldimethylsilyloxybenzenecarboxaldehyde, 7.2 g (24 mmol) of diethyl 4-ethoxycarbonylbenzylphosphonate and 885 mg of 12-crown-6 in 150 ml of THF was added dropwise and the mixture was stirred at room temperature for 8 hours. The reaction medium was poured into water and extracted with ethyl ether. The organic phase was separated out after settling had taken place, dried over magnesium sulfate and evaporated. The residue obtained was purified by chromatography on a column of silica, eluted with a mixture of ethyl acetate and heptane (5-95). After evaporation of the solvents, 4.8 g (46%) of ethyl (E)-4-[[2-[4-(1-adamantyl)-3-tert-butyldimethylsilyloxyphenyl]ethenyl]]benzoate, having a melting point of 140°–1° C. and 2.22 g (28%) of ethyl (E)-4-[[2-[4-(1-adamantyl)-3-hydroxyphenyl]ethenyl]]benzoate, having a melting point of 228°–9° C., were recovered.

(d) Synthesis of (E)-4-[[2-[4-(1-adamantyl)-3-hydroxyphenyl]ethenyl]]benzoic acid:

258 mg (0.5 mmol) of ethyl (E)-4-[[2-[4-(1-adamantyl)-3-hydroxyphenyl]ethenyl]]benzoate, 105 mg (2.5 mmol) of lithium hydroxide and 10 ml of THF were introduced into a round-bottomed flask. The reaction medium was stirred at room temperature for 12 hours, poured into water, neutralized with hydrochloric acid and extracted with ethyl ether. The organic phase was separated out after settling had taken place, dried over magnesium sulfate and evaporated. The residue obtained was triturated from a mixture of dichloromethane and hexane, filtered and dried. 95 mg (51%) of the expected acid, having a melting point of 334°–5° C., were recovered.

EXAMPLE 3

Preparation of (E)-4-[[2-[4-(1-adamantyl)-3-propyloxyphenyl]ethenyl]]benzoic acid (a) Preparation of ethyl (E)-4-[[2-[4-(1-adamantyl)-3-propyloxyphenyl]ethenyl]]benzoate:

66 mg (2.2 mmol) of sodium hydride (80% in oil) and 10 ml of DMF were introduced into a round-bottomed flask. A solution of 805 mg (2 mmol) of ethyl (E)-4-[[2-[4-(1-adamantyl)-3-hydroxyphenyl]ethenyl]]benzoate in 20 ml of DMF was added dropwise and the mixture was stirred until the evolution of gas has ceased. 200 μl (2.2 mmol) of 1-bromopropane were then added and the reaction medium was stirred at room temperature for 8 hours, poured into water and extracted with ethyl ether. The organic phase was separated out after settling had taken place, dried over magnesium sulfate and evaporated. The residue obtained was triturated from heptane, filtered and dried. 826 mg (93%) of the expected ethyl ester, having a melting point of 143°–4° C., were recovered.

(b) Synthesis of (E)-4-[[2-[4-(1-adamantyl)-3-propyloxyphenyl]ethenyl]]benzoic acid:

In a manner analogous to that of to Example 2(d), from 818 mg (1.84 mmol) of the above ethyl ester, 390 mg (51%) of the expected acid, having a melting point of 291°–3° C., were recoved.

EXAMPLE 4

Preparation of (E)-4-[[2-[4-(1-adamantyl)-3-heptyloxyphenyl]ethenyl]]benzoic acid (a) Preparation of ethyl (E)-4-[[2-[4-(1-adamantyl)-3-heptyloxyphenyl]ethenyl]]benzoate:

In a manner analogous to that of to Example 3(a), 805 mg (2 mmol) of ethyl (E)-4-[[2-[4-(1-adamantyl)-3-hydroxyphenyl]ethenyl]]benzoate were reacted with 346 μl (2.2 mmol) of 1-bromoheptane and 872 mg (87%) of the expected ethyl ester, having a melting point of 123°–4° C., were recovered.

(b) Synthesis of (E)-4-[[2-[4-(1-adamantyl)-3-heptyloxophenyl]ethenyl]]benzoic acid:

In a manner analogous to that of to Example 2(d), from 865 mg (1.73 mmol) of the above ethyl ester(a), 620 mg (76%) of the expected acid, having a melting point of 262°–3° C., were recoved.

EXAMPLE 5

Preparation of (E)-4-[[2-[4-(1-adamantyl)-3-methoxyphenyl]ethenyl]]benzoic acid (a) Preparation of ethyl (E)-4-[[2-[4-(1-adamantyl)-3-methoxyphenyl]ethenyl]]benzoate:

In a manner analogous to that of to Example 3(a), 805 mg (2 mmol) of ethyl (E)-4-[[2-[4-(1-adamantyl)-3-hydroxyphenyl]ethenyl]]benzoate were reacted with 137 μl (2.2 mmol) of methyl iodide and 768 mg (92%) of the expected ethyl ester, having a melting point of 152°–3° C., were recoved.

(b) Preparation of (E)-4-[[2-[4-(1-adamantyl)-3-methoxyphenyl]ethenyl]]benzoic acid:

In a manner analogous to that of to Example 2(d), from 763 mg (1.83 mmol) of the above ethyl ester, 615 mg (87%) of the expected acid, having a melting point of 284°–6° C., were recovered. 872 mg (87%) of the expected ethyl ester, having a melting point of 123°–4° C., were recovered.

(b) Synthesis of (E)-4-[[2-[4-(1-adamantyl)-3-heptyloxophenyl]ethenyl]]benzoic acid:

In a manner analogous to that of to Example 2(d), from 865 mg (1.73 mmol) of the above ethyl ester(a), 620 mg (76%) of the expected acid, having a melting point of 262°–3° C., were recoved.

EXAMPLE 5

Preparation of (E)-4-[[2-[4-(1-adamantyl)-3-methoxyphenyl]ethenyl]]benzoic acid (a) Preparation of ethyl (E)-4-[[2-[4-(1-adamantyl)-3-methoxyphenyl]ethenyl]]benzoate:

In a manner analogous to that of to Example 3(a), 805 mg (2 mmol) of ethyl (E)-4-[[2-[4-(1-adamantyl)-3-hydroxyphenyl]ethenyl]]benzoate were reacted with 137 μl (2.2 mmol) of methyl iodide and 768 mg (92%) of the expected ethyl ester, having a melting point of 152°–3° C., were recoved. (b) Preparation of (E)-4-[[2-[4-(1-adamantyl)-3-methoxyphenyl]ethenyl]]benzoic acid:

In a manner analogous to that of to Example 2(d), from 763 mg (1.83 mmol) of the above ethyl ester, 615 mg (87%) of the expected acid, having a melting point of 284°–6° C., were recovered.

EXAMPLE 6

Preparation of 4-[[2-[4-(1-adamantyl)-3-methoxyethoxymethoxyphenyl]ethynyl]]benzoic acid (a) Preparation of 4-(1-adamantyl)-3-methoxyethoxymethoxyphenylcarboxaldehyde:

18 g (45.5 mmol) of 4-(1-adamantyl)-1-bromo-3-methoxyethoxymethoxybenzene and 100 ml of THF were introduced into a three-necked flask under a stream of nitrogen. 20 ml of n-butyllithium solution (2.5M in hexane) were added dropwise, at −78° C., and the mixture was stirred for 30 min. 3.5 ml of DMF were then added dropwise and the mixture was permitted to warm to room temperature. The reaction medium was poured into aqueous ammonium chloride solution and extracted with ethyl ether. The organic phase was separated out after settling had taken place, dried over magnesium sulfate and evaporated. The residue obtained was purified by chromatography on a column of silica, eluted with a mixture of dichloromethane and heptane (30/70). After evaporation of the solvents, 12.7 g (81%) of the expected aldehyde, having a melting point of 87°–9° C., were recovered.

(b) Preparation of 2', 2'-dibromo-4-(1-adamantyl)-3-methoxyethoxymethoxystyrene:

5 g (14.5 mmol) of 4-(1-adamantyl)-3-methoxyethoxymethoxyphenylcarboxaldehyde and 30 ml of dichloromethane were introduced into a round-bottomed flask. 9.6 g (29 mmol) of carbon tetrabromide, 7.6 g (29 mmol) of triphenylphosphine and 1.9 g (29 mmol) of zinc powder were added successively and the mixture was stirred at room temperature for two hours. The reaction medium was evaporated and the residue obtained was purified by chromatography on a column of silica, eluted with a mixture of dichloromethane and heptane (40/60). 3 g (40%) of the expected compound were recovered.

(c) Preparation of 4-(1-adamantyl)-3-methoxyethoxymethoxyphenylacetylene:

3 g (6 mmol) of 2', 2'-dibromo-4-(1-adamantyl)-3-methoxyethoxymethoxystyrene and 50 ml of THF were introduced into a three-necked flask under a stream of nitrogen. 4.8 ml (12 mmol) of n-butyllithium solution (2.5M in hexane) were added dropwise, at –78° C., and the mixture was permitted to warm to room temperature over one hour. The reaction medium was poured into water and extracted with ethyl acetate. The organic phase was separated out after settling had taken place, dried over magnesium sulfate and evaporated. The residue was triturated from heptane, filtered and dried. 1.5 g (73%) of the expected acetylenic compound, having a melting point of 86°–8° C., was recovered.

(d) Preparation of methyl 4-[[2-[4-(1-adamantyl)-3-methoxyethoxymethoxyphenyl]ethynyl]]benzoate:

1.3 g (3.8 mmol) of 4-(1-adamantyl)-3-methoxyethoxymethoxyphenylacetylene, 1 g (3.8 mmol) of methyl 4-iodobenzoate and 15 ml of triethylamine were introduced into a three-necked flask. The reaction medium was degassed with nitrogen for 15 min, 100 mg of copper iodide and 260 mg (0.37 mmol) of bis(triphenylphosphine) palladium(II) chloride were added and the mixture was stirred at room temperature for twelve hours. The reaction medium was evaporated to dryness, the residue was taken up in water and ethyl ether and the organic phase was separated out after settling had taken place, dried over magnesium sulfate and evaporated. The residue obtained was purified by chromatography on a column of silica, eluted with a mixture of dichloromethane and heptane (20/80). After evaporation of the solvents, 1.3 g (72%) of the expected methyl ester was recovered.

(e) Synthesis of 4-[[2-[4-(1-adamantyl)-3-methoxyethoxymethoxyphenyl]ethynyl]]benzoic acid:

In a manner analogous to that of to Example 2(d), from 400 mg (0.8 mmol) of the above methyl ester (d), 250 mg (64%) of the expected acid, having a melting point of 215°–7° C., were recovered.

EXAMPLE 7

Preparation of (E)-4-[[2-[4-(1-adamantyl)-3-(5-carbamoylpentyloxy)phenyl]ethenyl]]benzoic acid (a) Preparation of ethyl (E)-4-[[2-[4-(1-adamantyl)-3-(5-carbamoylpentyloxy)phenyl]ethenyl]]benzoate:

805 mg (2 mmol) of ethyl (E)-4-[[2-[4-(1-adamantyl)-3-hydroxyphenyl]ethenyl]]benzoate, 388 mg (2 mmol) of 6-bromohexylamide, 331 mg of potassium carbonate and 30 ml of DMF were introduced into a round-bottomed flask. The reaction medium was heated at 70° C. for 3 days, poured into water and extracted with ethyl ether. The organic phase was separated out after settling had taken place, dried over magnesium sulfate and evaporated. The residue obtained was purified by chromatography on a column of silica, eluted with a mixture of ethyl acetate and heptane (80/20). After evaporation of the solvents, 586 mg (57%) of the expected ethyl ester, having a melting point of 160°–1° C., were recovered.

(b) Synthesis of (E)-4-[[2-[4-(1-adamantyl)-3-(5-carbamoylpentyloxy)phenyl]ethenyl]]benzoic acid:

575 mg (1.1 mol) of the above ethyl ester (a) and 20 ml of ethanol were introduced into a round-bottomed flask. 483 mg (12 mmol) of sodium hydroxide were added and the mixture was heated at 40° C. for 2 hours. The reaction medium was poured into water, acidified to pH 1 with hydrochloric acid and extracted with ethyl acetate. The organic phase was separated out after settling had taken place, dried over magnesium sulfate and evaporated. The solid obtained was triturated from a minimum amount of ethyl ether, filtered off and dried. 465 mg (88%) of the expected acid, having a melting point of 261°–2° C., were recovered.

EXAMPLE 8

Preparation of (E)-4-[[2-[4-(1-adamantyl)-3-methoxyphenyl]-1-propenyl]]benzoic acid (a) Preparation of 4-(1-adamantyl)-3-methoxyacetophenone:

7.3 g (25.5 mmol) of 4-(1-adamantyl)-3-methoxybenzoic acid and 300 ml of anhydrous ethyl ether were introduced into a three-necked flask under a stream of nitrogen. 32 ml (51 mmol) of methyllithium (1.6M in ether) were added dropwise, at –20° C., and the mixture was then stirred for three hours at room temperature. The reaction medium was poured into saturated aqueous ammonium chloride solution and the organic phase was separated out after settling had taken place, dried over magnesium sulfate and evaporated. The solid obtained was triturated from hexane, filtered off and dried. 5.05 g (70%) of the expected acetophenone, having a melting point of 101°–2° C., were recovered.

(b) Synthesis of (E)-4-[[2-[4-(1-adamantyl)-3-methoxyphenyl]-1-propenyl]]benzoic acid:

In a manner analogous to that of to Example 2(c), 1.9 g (6.6 mmol) of 4-(1-adamantyl)-3-methoxyacetophenone was reacted with 2.2 g (7.33 mmol) of diethyl 4-ethoxycarbonylbenzylphosphonate and 112 mg of (E)-4-[[2-[4-(1-adamantyl)-3-methoxyphenyl]-1-propenyl]] benzoic acid, having a melting point of 243°–5° C., were recovered.

EXAMPLE 9

Preparation of (E)-4-[[2-[4-(1-adamantyl)-3-(3-hydroxypropyloxy)phenyl]ethenyl]]benzoic acid (a) Preparation of methyl (E)-4-[[2-[4-(1-adamantyl)-3-(3-hydroxypropyloxy)phenyl]ethenyl]]benzoate:

In a manner analogous to that of to Example 7(a), 1 g (2.6 mmol) of methyl (E)-4-[[2-[4-(1-adamantyl)-3-hydroxyphenyl]ethenyl]]benzoate was reacted with 537 mg (3.8 mmol) of 3-bromopropanol and 472 mg (41%) of the expected methyl ester, having a melting point of 163°–5° C., were recovered.

(b) Synthesis of (E)-4-[[2-[4-(1-adamantyl)-3-(3-hydroxypropyloxy]phenyl]ethenyl]]benzoic acid:

In a manner analogous to that of to Example 7(b), from 464 mg (1.04 mmol) of the above methyl ester (a), 364 mg (84%) of the expected acid, having a melting point of 268°–70° C., were recovered.

EXAMPLE 10

Preparation of (E)-4-[[2-[4-(1-adamantyl)-3-(6-hydroxyhexyloxy)phenyl]ethenyl]]benzoic acid (a) Preparation of ethyl (E)-4-[[2-[4-(1-adamantyl)-3-(6-hydroxyhexyloxy)phenyl]ethenyl]]benzoate:

In a manner analogous to that of to Example 7(a), 1 g (2.5 mmol) of methyl (E)-4-[[2-[4-(1-adamantyl)-3-hydroxyphenyl]ethenyl]]benzoate was reacted with 710 mg (3.8 mmol) of 6-bromohexanol and 1.12 g (89%) of the expected methyl ester, having a melting point of 105°–7° C., was recovered.

(b) Synthesis of (E)-4-[[2-[4-(1-adamantyl)-3-(6-hydroxyhexyloxy)phenyl]ethenyl]]benzoic acid:

In a manner analogous to that of to Example 7(b), from 1.09 g (2.23 mmol) of the above methyl ester (a), 943 mg (89%) of the expected acid, having a melting point of 238°–40° C., were recovered.

EXAMPLE 11

Preparation of 4-[[3-oxo-3-[4-(1-adamantyl)-3-methoxyphenyl]-1-propenyl]]benzoic acid (a) Preparation of 2-(1-adamantyl)-5-bromophenol:

41 g (0.237 mol) of 3-bromophenol, 38 g (0.25 mol) of 1-adamantanol and 500 ml of dichloromethane were introduced into a round-bottomed flask. 12.5 ml of concentrated sulfuric acid were added and the mixture was stirred at room temperature for eight hours. The reaction medium was poured into water and the organic phase was separated out after settling had taken place, washed with water, dried over magnesium sulfate and evaporated. The residue obtained was purified by chromatography on a column of silica, eluted with dichloromethane. After evaporation of the solvents, 45 g (62%) of the expected phenol, having a melting point of 112°–4° C., were recovered.

(b) Preparation of 2-(1-adamantyl)-5-bromoanisole:

20 g (65 mmol) of 2-(1-adamantyl)-5-bromophenol and 200 ml of DMF were introduced into a three-necked flask under a stream of nitrogen. 1.9 g (65 mmol) of sodium hydride (80% in oil) was added portionwise and the mixture was stirred until the evolution of gas had ceased. 5.3 ml (84.5 mmol) of iodomethane were then added and the mixture was stirred at room temperature for three hours. The reaction medium was poured into water and extracted with ethyl ether. The organic phase was separated out after settling had taken place, washed with water, dried over magnesium sulfate and evaporated. 20.8 g (100%) of the expected compound were recovered.

(c) Preparation of 4-(1-adamantyl)-3-methoxybenzoic acid:

The above compound (b) (11.3 g, 35 mmol) was dissolved in 200 ml of THF. The solution obtained was added dropwise to magnesium (1.3 g, 52.5 mmol) and a crystal of iodine. After introduction, the mixture was heated at reflux for two hours, cooled to −78° C. and a stream of $CO_2$ was passed therethrough for one hour. The reaction medium was permitted to warm to room temperature, poured into saturated aqueous ammonium chloride solution and extracted with ethyl ether. The organic phase was separated out after settling had taken place, dried over magnesium sulfate and evaporated. The residue obtained was purified by chromatography on a column of silica, eluted with a mixture of dichloromethane and ethyl ether (90/10). 5.1 g (51%.) of the expected acid, having a melting point of 259°–60° C., were recovered.

(d) Preparation of 4-(1-adamantyl)-3-methoxyacetophenone:

2.8 g (10 mmol) of 4-(1-adamantyl)-3-methoxybenzoic acid and 100 ml of anhydrous ethyl ether were introduced into a three-necked flask under a stream of nitrogen. 15.3 ml (25 mmol) of methyllithium (1.6M in ether) were added dropwise, at −20° C., and the mixture was then stirred for three hours at room temperature. The reaction medium was poured into saturated aqueous ammonium chloride solution and the organic phase was separated out after settling had taken place, dried over magnesium sulfate and evaporated. 2.5 g (90%) of the expected acetophenone, having a melting point of 89°–90° C., were recovered.

(e) Synthesis of 4-[[3-oxo-3-[4-(1-adamantyl)-3-methoxyphenyl]-1-propenyl]]benzoic acid:

1.4 g (4.9 mmol) of 4-(1-adamantyl)-3-methoxyacetophenone, 810 mg (4.9 mmol) of 4-formylbenzoic acid and 100 ml of methanol were introduced into a round-bottomed flask. 20 ml (20 mmol) of sodium hydroxide solution (1N) were added and the mixture was stirred at room temperature for twelve hours. The reaction medium was evaporated to dryness and the residue was taken up in water, acidified to pH 1 and extracted with ethyl ether. The organic phase was separated out after settling had taken place, dried over magnesium sulfate and evaporated. The solid was triturated from diisopropyl ether, filtered off and dried. 480 mg of 4-[[3-oxo-3-[4-(1-adamantyl)-3-methoxyphenyl]-1-propenyl]]benzoic acid, having a melting point of 277°–9° C., were recovered.

EXAMPLE 12

Preparation of 4-[4-(1-adamantyl)-3-methoxyethoxymethoxybenzoylthio]benzoic acid (a) Preparation of 4-(1-adamantyl)-1-bromo-3-methoxyethoxymethoxybenzene:

In a manner analogous to that of to Example 11(b), 72.94 g (0.237 mol) of 2-(1-adamantyl)-5-bromophenol were reacted with 32.5 ml (0.284 ml) of methoxyethoxymethyl chloride and 86.9 g (93%) of 4-(1-adamantyl)-1-bromo-3-methoxyethoxymethoxybenzene, having a melting point of 72°–3° C., were recovered.

(b) Preparation of 4-(1-adamantyl)-3-methoxyethoxymethoxybenzoic acid:

43.5 g (0.11 mol) of 4-(1-adamantyl)-1-bromo-3-methoxyethoxymethoxybenzene and 450 ml of THF were introduced into a three-necked flask under a stream of nitrogen. 48 ml (0.12 mol) of n-butyllithium solution (2.5M in hexane) were added dropwise, at −78° C. and the mixture was stirred at this temperature for one hour. A stream of $CO_2$ was introduced at −70° C. for 30 min and the mixture was permitted to warm to room temperature. The reaction medium was poured into saturated ammonium chloride solution and extracted with ethyl acetate. The organic phase was separated out after settling had taken place, dried over magnesium sulfate and evaporated. The solid obtained was triturated from hexane, filtered off and dried. 27.8 g (82%) of the expected acid, having a melting point of 145°–7° C., were recovered.

(c) Preparation of 4-(1-adamantyl)-3-methoxyethoxymethoxybenzoyl chloride:

A solution of 8 g (22 mmol) of 4-(1-adamantyl)-3-methoxyethoxymethoxybenzoic acid in 80 ml of anhydrous dichloromethane was introduced into a round-bottomed flask and 4.45 ml (22 mmol) of dicyclohexylamine were added, and the mixture was stirred for one hour. 1.6 ml (22 mmol) of thionyl chloride was then added and the mixture was stirred for one hour. It was evaporated to dryness, the residue was taken up in anhydrous ethyl ether, the dicyclohexylamine salt was filtered off and the filtrate was evaporated. 8.5 g (100%) of the crude acid chloride, which was used without further purification in the remainder of the synthesis, were recovered.

(d) Synthesis of 4-[4-(1-adamantyl)-3-methoxyethoxymethoxybenzoylthio]benzoic acid:

850 mg (5.5 mmol) of 4-mercaptobenzoic acid and 20 ml of pyridine were introduced into a round-bottomed flask. A solution of 2.08 g (5.5 mmol) of 4-(1-adamantyl)-3-methoxyethoxymethoxybenzoyl chloride prepared above was added dropwise and the mixture was stirred at room temperature for six hours. It was evaporated to dryness and the residue was taken up in water and ethyl acetate and acidified to pH 5, and the organic phase was separated out after settling had taken place, washed with water, dried over magnesium sulfate and evaporated. The solid obtained was purified by chromatography on a column of silica, eluted with a mixture of dichloromethane and methanol (98/2). 1.5 g (57%) of 4-[4-(1-adamantyl)-3-methoxyethoxymethoxybenzoylthio]benzoic acid, having a melting point of 219°–21° C., was recovered.

EXAMPLE 13

Preparation of 4-[4-(1-adamantyl)-3-methoxyethoxymethoxybenzoyloxy]benzoic acid (a) Preparation of allyl 4-[4-(1-adamantyl)-3-methoxyethoxymethoxybenzoyloxy]benzoate:

1.26 g (5.5 mmol) of benzyl 4-hydroxybenzoate and 20 ml of THF were introduced into a three-necked flask under a stream of nitrogen. 181 mg (6.1 mmol) of sodium hydride (80% in oil) were added portionwise and the mixture was stirred until the evolution of gas had ceased. A solution of 2.08 g (5.5 mmol) of 4-(1-adamantyl)-3-methoxyethoxymethoxybenzoyl chloride prepared in Example 12(c) was then added dropwise and the mixture was stirred at room temperature for six hours. The reaction medium was poured into water and extracted with ethyl ether. The organic phase was separated out after settling had taken place, dried over magnesium sulfate and evaporated. The solid obtained was triturated from a mixture of hexane and ethyl ether, filtered off and dried. 2.47 g (79%) of the expected benzyl ester, having a melting point of 107°–8° C., were recovered.

(b) Synthesis of 4-[4-(1-adamantyl)-3-methoxyethoxymethoxybenzoyloxy]benzoic acid:

2.46 g (4.3 mmol) of allyl 4-[4-(1-adamantyl)-3-methoxyethoxymethoxybenzoyloxy]benzoate, 40 ml of dioxane and 492 mg of palladium-on-charcoal (10%) were introduced into a reactor. The mixture was hydrogenated at 40° C. and at a pressure of 7 bar for three hours. The catalyst was filtered off and the filtrate was evaporated to dryness. The solid obtained was recrystallized from methanol, filtered off and dried. 1.57 g (76%) of the expected acid, having a melting point of 212°–4° C., was recovered.

EXAMPLE 14

Preparation of 4-[4-(1-adamantyl)-3-methoxyethoxymethoxybenzamido]benzoic acid (a) Preparation of allyl 4-[4-(1-adamantyl)-3-methoxyethoxymethoxybenzamido]benzoate:

1.95 g (11 mmol) of allyl 4-aminobenzoate, 1.7 ml (12 mmol) of triethylamine and 50 ml of THF were introduced into a round-bottomed flask. A solution of 4.16 g (11 mmol) of 4-(1-adamantyl)-3-methoxyethoxymethoxybenzoyl chloride was added dropwise and the mixture was stirred at room temperature for 4 hours. The reaction medium was poured into water and extracted with ethyl ether. The organic phase was separated out after settling had taken place, dried over magnesium sulfate and evaporated. The residue obtained was purified by chromatography on a column of silica, eluted with dichloromethane. 4.45 g (78%) of the expected allylic ester were recovered in the form of an oil.

(b) Synthesis of 4-[4-(1-adamantyl)-3-methoxyethoxymethoxybenzamido]benzoic acid:

107 mg (3.5 mmol) of sodium hydride (80% in oil) and 5 ml of THF were introduced into a round-bottomed flask under a stream of nitrogen. 535 µl (3.5 mmol) of diethyl malonate were then added dropwise and the mixture was stirred until the evolution of gas had ceased. This solution was introduced dropwise into a mixture of 1.67 g (3.2 mmol) of allyl 4-[4-(1-adamantyl)-3-methoxyethoxymethoxybenzamido]benzoate, 40 ml of THF and 184 mg (0.18 mmol) of tetrakis(triphenylphosphine)palladium(0) and the mixture was stirred at room temperature for three hours. The reaction medium was poured into water and extracted with ethyl ether. The organic phase was separated out after settling had taken place, dried over magnesium sulfate and evaporated. The residue obtained was purified by chromatography on a column of silica, eluted with a mixture of dichloromethane and ethyl acetate (80/20). After evaporation of the solvents, 630 mg (41%) of 4-[4-(1-adamantyl)-3-methoxyethoxymethoxybenzamido]benzoic acid, having a melting point of 189°–91° C., were recovered.

EXAMPLE 15

Preparation of (E)-4-[2-(4-(1-adamantyl)-3-methoxyethoxymethoxyphenyl)ethenyl]benzoic acid (a) Preparation of 4-(1-adamantyl)-3-methoxyethoxymethoxybenzaldehyde:

43.1 g (0.109 mol) of 4-(1-adamantyl)-1-bromo-3-methoxyethoxymethoxybenzene and 450 ml of THF were introduced into a three-necked flask under a stream of nitrogen. 48 ml (0.12 mol) of n-butyllithium solution (2.5M in hexane) were added dropwise, at −78° C., and the mixture was stirred at this temperature for one hour. 9.25 ml (0.12 mol) of DMF were then introduced, at −70° C., and the mixture was permitted to warm to room temperature. The reaction medium was poured into saturated ammonium chloride solution and extracted with ethyl acetate. The organic phase was separated out after settling had taken place, dried over magnesium sulfate and evaporated. The residue obtained was purified by chromatography on a column of silica, eluted with dichloromethane. 27.8 g (74%) of the expected aldehyde, having a melting point of 87°–9° C., were recovered.

(b) Preparation of methyl (E)-4-[2-(4-(1-adamantyl)-3-methoxyethoxymethoxyphenyl)ethenyl]benzoate:

1.72 g (5 mmol) of 4-(1-adamantyl)-3-methoxyethoxymethoxybenzaldehyde, 1.55 g (6 mmol) of dimethyl 4-methoxycarbonylbenzylphosphonate, 40 ml of THF and 224 mg of crown ether (15-crown-5) were introduced into a three-necked flask under a stream of nitrogen. 181 mg (6 mmol) of sodium hydride (80% in oil) were then added portionwise and the mixture was stirred at room temperature for twelve hours. The reaction medium was poured into water and extracted with ethyl ether. The organic phase was separated out after settling had taken place, dried over magnesium sulfate and evaporated. The residue obtained was purified by chromatography on a column of silica, eluted with dichloromethane. 1.82 g (76%) of the expected methyl ester, having a melting point of 113°–4° C., was recovered.

(c) Synthesis of (E)-4-[2-(4-(1-adamantyl)-3-methoxyethoxymethoxyphenyl)ethenyl]benzoic acid:

1.8 g (3.8 mmol) of the above methyl ester (b) 1.5 g (38 mmol) of sodium hydroxide and 50 ml of methanol were introduced into a round-bottomed flask. The reaction medium was heated at reflux for three hours and is then evaporated to dryness. The residue obtained was taken up in water, acidified to pH 1 and extracted with ethyl acetate. The organic phase was separated out after settling had taken place, dried over magnesium sulfate and evaporated. The solid was triturated from a minimum amount of ethyl ether, filtered off and dried. 1.63 g (93%) of (E)-4-[2-(4-(1-adamantyl)-3-methoxyethoxymethoxyphenyl)ethenyl]benzoic acid, having a melting point of 219°–21° C., was recovered.

EXAMPLE 16

Preparation of (E)-4-[2-(4-(1-adamantyl)-3-methoxyethoxymethoxyphenyl)-1-propenyl]benzoic acid (a) Preparation of 4-(1-adamantyl)-3-methoxyethoxymethoxyacetophenone:

19.8 g (55 mmol) of 4-(1-adamantyl)-3-methoxyethoxymethoxybenzoic acid and 200 ml of anhydrous ethyl ether were introduced into a three-necked flask under a stream of nitrogen. 70 ml (0.13 mol) of methyl-lithium (1.6M in ether) were added dropwise, at –20° C., and the mixture was then stirred for three hours at room temperature. The reaction medium was poured into saturated aqueous ammonium chloride solution and the organic phase was separated out after settling had taken place, dried over magnesium sulfate and evaporated. 19.7 g (100%) of the expected acetophenone were recovered in the form of a pale yellow oil.

(b) Preparation of methyl (E)-4-[2-(4-(1-adamantyl)-3-methoxyethoxymethoxyphenyl)-1-propenyl]benzoate:

In a manner analogous to that of to Example 15(b), 3.58 g (10 mmol) of 4-(1-adamantyl)-3-methoxyethoxymethoxyacetophenone were reacted with 3.13 g (12 mmol) of dimethyl 4-methoxycarbonylbenzylphosphonate, and after chromatography on a column of silica, eluted with a mixture of heptane and ethyl acetate (80/20), 380 mg (15%) of methyl (E)-4-[2-(4-(1-adamantyl)-3-methoxyethoxymethoxyphenyl)-1-propenyl]benzoate, having a melting point of 84°–6° C., and 550 mg (22%) of methyl (Z)-4-[2-(4-(1-adamantyl)-3-methoxyethoxymethoxyphenyl)-1-propenyl]benzoate, having a melting point of 77°–8° C., were recovered.

(c) Synthesis of (E)-4-[2-(4-(1-adamantyl)-3-methoxyethoxymethoxophenyl)-1-propenyl]benzoic acid:

In a manner analogous to that of to Example 15(c), from 330 mg (0.67 mmol) of methyl (E)-4-[2-(4-(1-adamantyl)-3-methoxyethoxymethoxyphenyl)-1-propenyl]benzoate, 243 mg (76%) of (E)-4-[2-(4-(1-adamantyl)-3-methoxyethoxymethoxyphenyl)-1-propenyl]benzoic acid, having a melting point of 193°–4° C., were recovered.

EXAMPLE 17

Preparation of (Z)-4-[2-(4-(1-adamantyl)-3-methoxyethoxymethoxyphenyl)-1-propenyl]benzoic acid In a manner analogous to that of to Example 15(c), from 540 mg (1.1 mmol) of methyl (Z)-4-[2-(4-(1-adamantyl)-3-methoxyethoxymethoxyphenyl)-1-propenyl]benzoate, 437 mg (83%) of (Z)-4-[2-(4-(1-adamantyl)-3-methoxyethoxymethoxyphenyl)-1-propenyl]benzoic acid, having a melting point of 191°–2° C., were recovered.

EXAMPLE 18

Preparation of 4-[4-(1-adamantyl)-3-methoxyethoxymethoxybenzoylmethyloxy]benzoic acid (a) Preparation of 2'-bromo-4-(1-adamantyl)-3-hydroxyacetophenone:

4.47 g (20 mmol) of CuBr$_2$ and 45 ml of chloroform were introduced into a round-bottomed flask. The mixture was heated to reflux and a solution of 3.57 g (10 mmol) of 4-(1-adamantyl)-3-methoxyethoxymethoxyacetophenone in 50 ml of ethyl acetate was added dropwise. The reaction medium was maintained at reflux for four hours and was then filtered and evaporated to dryness. The residue was purified by chromatography on a column of silica, eluted with dichloromethane. 2.51 g (72%) of 2'-bromo-4-(1-adamantyl)-3-hydroxyacetophenone, having a melting point of 200°–2° C., were recovered.

(b) Preparation of methyl 4-[4-(1-adamantyl)-3-hydroxybenzoylmethyloxy]benzoate:

2.15 g (6.1 mmol) of 2'-bromo-4-(1-adamantyl)-3-hydroxyacetophenone, 934 mg of methyl 4-hydroxybenzoate, 1 g (7.37 mmol) of potassium carbonate and 60 ml of methyl ethyl ketone were introduced into a round-bottomed flask. The reaction medium was heated at reflux for four hours, poured into hydrochloric acid (1N) and extracted with ethyl ether. The organic phase was separated out after settling had taken place, dried over magnesium sulfate and evaporated. The residue obtained was purified by chromatography on a column of silica, eluted with a mixture of heptane and ethyl acetate (70/30). 1.55 g (69%) of the expected product, having a melting point of 209°–10° C., was recovered.

(c) Preparation of methyl 4-[4-(1-adamantyl)-3-methoxyethoxymethoxybenzoylmethyloxylbenzoate:

In a manner analogous to that of to Example 11(b), 472 mg (1.12 mmol) of methyl 4-[4-(1-adamantyl)-3-hydroxybenzoylmethyloxy]benzoate were reacted with 154 µl (1.35 mmol) of methoxyethoxymethyl chloride and 217 mg (38%) of the expected methyl ester were recovered in the form of a yellow oil.

(d) Synthesis of 4-[4-(1-adamantyl)-3-methoxyethoxymethoxybenzoylmethyloxy]benzoic acid:

In a manner analogous to that of to Example 15(c), from 551 mg (1.08 mmol) of the above methyl ester (c), 230 mg (46%) of 4-[4-(1-adamantyl)-3-methoxyethoxymethoxybenzoylmethyloxy]benzoic acid, having a melting point of 235°–6° C., were recovered.

EXAMPLE 19

Preparation of 4-[[3-oxo-3-[4-(1-adamantyl)-3-methoxyethoxymethoxophenyl]-1-propenyl]]benzoic acid 1.8 g (5 mmol) of 4-(1-adamantyl)-3-methoxyethoxymethoxyacetophenone prepared in Example 16(a), 820 mg (5 mmol) of methyl 4-formylbenzoate and 20 ml of methanol were introduced into a round-bottomed flask. 10 mg of 18-crown-6 and 200 mg of sodium hydroxide pellets were added and the mixture was stirred at room temperature for 4 hours. It was evaporated to dryness and the residue was taken up in water, acidified to pH 3 with hydrochloric acid (1N) and extracted with ethyl ether. The organic phase was separated out after settling had taken place, dried over magnesium sulfate and evaporated. The residue obtained was purified by chromatography on a column of silica, eluted with dichloromethane. 432 mg (17%) of methyl 4-[[3-oxo-3-[4-(1-adamantyl)-3-methoxyethoxymethoxyphenyl]-1-propenyl]]benzoate, having a melting point of 95°–6° C., and 636 mg (26%) of 4-[[3-oxo-3-[4-(1-adamantyl)-3-methoxyethoxymethoxyphenyl]-1-propenyl]]benzoic acid, having a melting point of 183°–5° C., were recovered.

EXAMPLE 20

Preparation of 4-[[3-hydroxy-3-[4-(1-adamantyl)-3-methoxyethoxymethoxyphenyl]-1-propenyl]]benzoic acid (a) Preparation of methyl 4-[[3-hydroxy-3-[4-(1-adamantyl)-3-methoxyethoxymethoxyphenyl]-1-propenyl]]benzoate:

425 mg (0.84 mmol) of methyl 4-[[3-oxo-3-[4-(1-adamantyl)-3-methoxyethoxymethoxyphenyl]-1-propenyl]] benzoate obtained in Example 19, 246 mg of cerium chloride and 10 ml of methanol were introduced into a round-bottomed flask. The mixture was stirred at room temperature for one hour and 16 mg (0.42 mmol) of sodium borohydride were then added and the mixture was stirred for four hours. It was evaporated to dryness and the residue was taken up in water and extracted with ethyl ether. The organic phase was separated out after settling had taken place, dried over magnesium sulfate and evaporated. The residue obtained was purified by chromatography on a column of silica, eluted with dichloromethane. 344 mg (81%) of the expected methyl ester were recovered in the form of an oil.

(b) Synthesis of 4-[[3-hydroxy-3-[4-(1-adamantyl)-3-methoxyethoxymethoxyphenyl]-1-propenyl]]benzoic acid:

In a manner analogous to that of to Example 15(c), from 308 mg (0.61 mmol) of the above methyl ester, 91 mg (30%) of 4-[[3-hydroxy-3-[4-(1-adamantyl)-3-methoxyethoxymethoxyphenyl]-1-propenyl]]benzoic acid, having a melting point of 127°–9° C., were recovered.

EXAMPLE 21

Preparation of allyl 4-[4-(1-adamantyl)-3-methoxyethoxymethoxythiobenzamido]benzoate 2.9 g (5.6 mmol) of allyl 4-[4-(1-adamantyl)-3-methoxyethoxymethoxybenzamido]benzoate and 30 ml of toluene were introduced into a round-bottomed flask and 1.14 g (2.8 mmol) of Lawesson's reagent were added. The reaction medium was heated at reflux for three hours and was then evaporated to dryness. The residue obtained was taken up in water and dichloromethane and the organic phase was separated out after settling had taken place, dried over magnesium sulfate and evaporated. The residue obtained was purified by chromatography on a column of silica, eluted with a mixture of heptane and ethyl acetate (80/20). After evaporation of the solvents, 1 g (33%) of the expected allylic ester was collected in the form of an orange-coloured oil.

EXAMPLE 22

In this example, various specific formulations based on the compounds according to the invention are illustrated.

(A) ORAL ROUTE:

(a) 0.2 g Tablets:

| | | |
|---|---|---|
| (i) | compound of Example 1 | 0.001 g |
| (ii) | Starch | 0.114 g |
| (iii) | Dicalcium phosphate | 0.020 g |
| (iv) | Silica | 0.020 g |
| (v) | Lactose | 0.030 g |
| (vi) | Talc | 0.010 g |
| (vii) | Magnesium stearate | 0.005 g |

(b) Drinkable suspension in 5 ml ampules:

| | | |
|---|---|---|
| (i) | Compound of Example 2 | 0.001 g |
| (ii) | Glycerol | 0.500 g |
| (iii) | 70% Sorbitol | 0.500 g |
| (iv) | Sodium saccharinate | 0.010 g |
| (v) | Methyl para-hydroxybenzoate | 0.040 g |
| (vi) | Flavoring | qs |
| (vii) | Purified water qs | 5 ml |

(c) 0.8 g Tablets:

| | | |
|---|---|---|
| (i) | Compound of Example 6 | 0.500 g |
| (ii) | Pregelatinized starch | 0.100 g |
| (iii) | Microcrystalline cellulose | 0.115 g |
| (iv) | Lactose | 0.075 g |
| (v) | Magnesium stearate | 0.010 g |

(d) Drinkable suspension in 10 ml ampules:

| | | |
|---|---|---|
| (i) | Compound of Example 4 | 0.05 g |
| (ii) | Glycerol | 1.000 g |
| (iii) | 70% Sorbitol | 1.000 g |
| (iv) | Sodium saccharinate | 0.010 g |
| (v) | Methyl para-hydroxybenzoate | 0.080 g |
| (vi) | Flavoring | qs |
| (vii) | Purified water qs | 10 ml |

(B) TOPICAL ROUTE:

(a) Ointment:

| | | |
|---|---|---|
| (i) | Compound of Example 1 | 0.020 g |
| (ii) | Isopropyl myristate | 81.700 g |
| (iii) | Fluid liquid petrolatum | 9.100 g |
| (iv) | Silica ("Aerosil 200" marketed by Degussa) | 9.180 g |

(b) Ointment:

| | | |
|---|---|---|
| (i) | Compound of Example 6 | 0.300 g |
| (ii) | White petrolatum codex | 100 g |

(c) Nonionic water-in-oil cream:

| | | |
|---|---|---|
| (i) | Compound of Example 1 | 0.100 g |
| (ii) | Mixture of emulsifying lanolin alcohols, waxes and oils ("anhydrous eucerin") sold by BDF | 39.900 g |
| (iii) | Methyl para-hydroxybenzoate | 0.075 g |
| (iv) | Propyl para-hydroxybenzoate | 0.075 g |
| (v) | Sterile demineralized water qs | 100 g |

(d) Lotion:

| | | |
|---|---|---|
| (i) | Compound of Example 1 | 0.100 g |
| (ii) | Polyethylene glycol (PEG 400) | 69.900 g |
| (iii) | 95% Ethanol | 30.000 g |

(e) Hydrophobic ointment:

| | | |
|---|---|---|
| (i) | Compound of Example 2 | 0.300 g |
| (ii) | Isopropyl myristate | 36.400 g |
| (iii) | Silicone oil ("Rhodorsil 47 V 300" marketed by Rhône-Poulenc) | 36.400 g |
| (iv) | Beeswax | 13.600 g |
| (v) | Silicone oil ("Abil 300,000 cst" marketed by Goldschmidt) | 100 g |

(f) Nonionic oil-in-water cream:

| | | |
|---|---|---|
| (i) | Compound of Example 4 | 0.500 g |
| (ii) | Cetyl alcohol | 4.000 g |
| (iii) | Glyceryl monostearate | 2.500 g |
| (iv) | PEG 50 stearate | 2.500 g |

-continued

| (v) | Karite butter | 9.200 g |
| (vi) | Propylene glycol | 2.000 g |
| (vii) | Methyl para-hydroxybenzoate | 0.075 g |
| (viii) | Propyl para-hydroxybenzoate | 0.075 g |
| (ix) | Sterile demineralized water | 100 g |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. An adamantyl-substituted biaromatic compound having the structural formula (I):

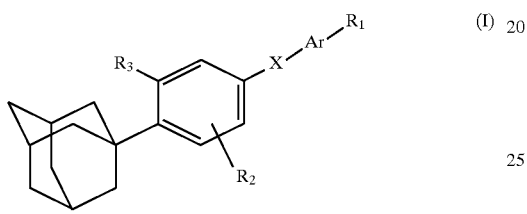

in which $R_1$ is a —$CH_3$ radical, a —$(CH_2)n$—O—$R_4$ radical, an —O—$(CH_2)m$—$(CO)n$—$R_5$ radical, a —CO—$R_6$ radical, or a —CO—O—$R_7$ radical, wherein values of m and n and the radicals $R_4$ to $R_7$ are as defined below; $R_2$ is a hydrogen atom, a halogen atom, a linear or branched alkyl radical having from 1 to 20 carbon atoms, an —$OR_4$ radical, or an —O—$CH_2$—O—$CH_2$—$CH_2$—O—$CH_3$ radical; $R_3$ is a —Y—$(CH_2)p$—Y—$(CH_2)q$—$R_8$ radical, a —$(CH_2)p$—$(Y)_s$—$(CH_2)q$—$R_8$ radical, a —Y—$(CH_2)q$—$R_8$ radical, or a —CH=CH—$(CH_2)r$—$R_8$ radical, wherein the values of p, g, r and s and the radicals Y and $R_8$ are as defined below; X is a bridging radical selected from among those of the following formulae (a)–(m), which may be oriented left-to-right or right-to-left:

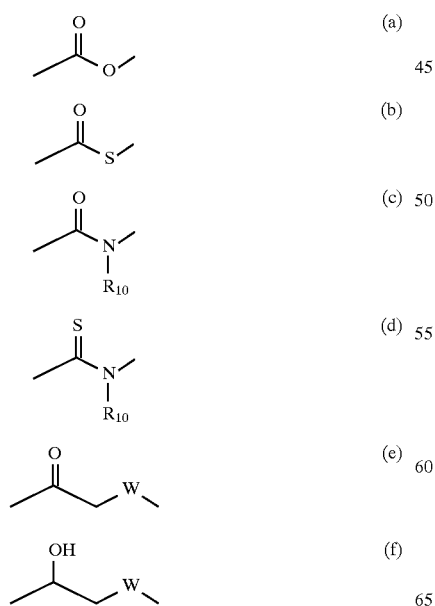

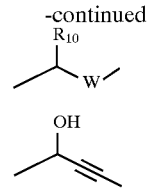

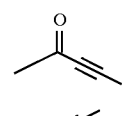

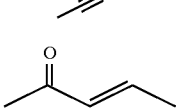

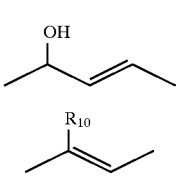

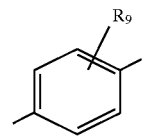

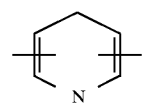

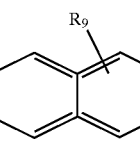

Ar is a radical selected from among those of the following formulae (a')–(f'):

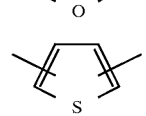

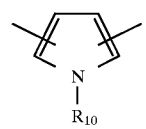

m is an integer equal to 1, 2 or 3; n is an integer equal to 0 or 1; p is an integer ranging from 1 to 12, inclusive; q is an integer ranging from 0 to 12, inclusive; r is an integer ranging from 0 to 10, inclusive; s is an integer equal to 0 or 1; t is an integer equal to 0, 1 or 2; Y is an oxygen atom or a radical S(O)t; W is an oxygen atom, a radical S(O)t or a radical N—$R_{10}$; $R_4$ is a hydrogen atom, a lower alkyl radical or a radical —CO—$R_{11}$; $R_5$ is a lower alkyl radical or a heterocycle; $R_6$ is a hydrogen atom, a lower alkyl radical, or a radical

in which R' and R", which may be identical or different, are each a hydrogen atom, a lower alkyl radical, a mono- or polyhydroxyalkyl radical, an optionally substituted aryl radical, or an amino acid or peptide or sugar residue, with the proviso that R' and R" may together form, with the nitrogen atom from which they depend, a nitrogen-containing heterocycle; $R_7$ is a hydrogen atom, a linear or branched alkyl radical having from 1 to 20 carbon atoms, an alkenyl radical, a mono- or polyhydroxyalkyl radical, an optionally substituted aryl or aralkyl radical, or a sugar residue or an amino acid or peptide residue; $R_8$ is a hydrogen atom, a branched alkyl radical having from 1 to 20 carbon atoms, a C3–C6 cycloaliphatic radical, a monohydroxyalkyl radical or a polyhydroxyalkyl radical, said hydroxyls optionally being protected as methoxy, acetoxy or acetonide groups, an aryl radical, an alkenyl radical, an alkynyl radical, a —CO—$R_6$ radical, a —CO—O—$R_7$ radical, an amino alkyl radical whose amine function is optionally substituted with one or two lower alkyl radicals, or a heterocycle, wherein $R_7$ is as defined above; $R_9$ is a hydrogen or halogen atom, a linear or branched alkyl radical having from 1 to 20 carbon atoms, an —$OR_4$ radical or an —O—$CH_2$—O—$CH_2$—$CH_2$—O—$CH_3$ radical; the radicals $R_{10}$, which may be identical or different, are each a hydrogen atom or a lower alkyl radical; and $R_{11}$ is a lower alkyl radical, with the proviso that, when X is a bridging radical of formula (e) and $R_3$ is a radical —Y—$(CH_2)q$—$R_8$ wherein Y is an oxygen atom and $R_8$ is a hydrogen atom, then q must be greater than 6; or a pharmaceutically/cosmetically acceptable derivative or optical or geometric isomer thereof.

2. The adamantyl-substituted biaromatic compound as defined by claim 1, wherein formula (I), Ar has the structure (a').

3. The adamantyl-substituted biaromatic compound as defined by claim 1, wherein formula (I), Ar has the structure (b').

4. The adamantyl-substituted biaromatic compound as defined by claim 1, wherein formula (I), Ar has the structure (c').

5. The adamantyl-substituted biaromatic compound as defined by claim 1, wherein formula (I), Ar has the structure (d').

6. The adamantyl-substituted biaromatic compound as defined by claim 1, wherein formula (I), Ar has the structure (e').

7. The adamantyl-substituted biaromatic compound as defined by claim 1, wherein formula (I), Ar has the structure (f').

8. The adamantyl-substituted biaromatic compound as defined by claim 1, wherein formula (I), X has the structure (a).

9. The adamantyl-substituted biaromatic compound as defined by claim 1, wherein formula (I), X has the structure (b).

10. The adamantyl-substituted biaromatic compound as defined by claim 1, wherein formula (I), X has the structure (c).

11. The adamantyl-substituted biaromatic compound as defined by claim 1, wherein formula (I), X has the structure (d).

12. The adamantyl-substituted biaromatic compound as defined by claim 1, wherein formula (I), X has the structure (e).

13. The adamantyl-substituted biaromatic compound as defined by claim 1, wherein formula (I), X has the structure (f).

14. The adamantyl-substituted biaromatic compound as defined by claim 1, wherein formula (I), X has the structure (g).

15. The adamantyl-substituted biaromatic compound as defined by claim 1, wherein formula (I), X has the structure (h).

16. The adamantyl-substituted biaromatic compound as defined by claim 1, wherein formula (I), X has the structure (i).

17. The adamantyl-substituted biaromatic compound as defined by claim 1, wherein formula (I), X has the structure (j).

18. The adamantyl-substituted biaromatic compound as defined by claim 1, wherein formula (I), X has the structure (k).

19. The adamantyl-substituted biaromatic compound as defined by claim 1, wherein formula (I), X has the structure (l).

20. The adamantyl-substituted biaromatic compound as defined by claim 1, wherein formula (I), X has the structure (m).

21. The adamantyl-substituted biaromatic compound as defined by claim 1, comprising a pharmaceutically acceptable salt thereof.

22. The adamantyl-substituted biaromatic compound as defined by claim 1, comprising at least one lower alkyl radical substituent selected from among methyl, ethyl, isopropyl, butyl, tert-butyl, hexyl, nonyl and dodecyl radicals.

23. The adamantyl-substituted biaromatic compound as defined by claim 1, comprising at least one linear alkyl radical substituent selected from among methyl, ethyl, propyl, 2-ethylhexyl, octyl, dodecyl, hexadecyl and octadecyl radicals.

24. The adamantyl-substituted biaromatic compound as defined by claim 1, comprising at least one branched alkyl radical substituent selected from among 2-methylbutyl, 2-methylpentyl, 1-methylhexyl and 3-methylheptyl radicals.

25. The adamantyl-substituted biaromatic compound as defined by claim 1, comprising at least one monohydroxyalkyl radical substituent selected from among 2-hydroxyethyl, 2-hydroxypropyl and 3-hydroxypropyl radicals.

26. The adamantyl-substituted biaromatic compound as defined by claim 1, comprising at least one polyhydroxyalkyl radical substituent selected from among 2,3-dihydroxypropyl, 2,3,4-trihydroxybutyl and 2,3,4,5-tetrahydroxypentyl radicals, and the pentaerythritol residue.

27. The adamantyl-substituted biaromatic compound as defined by claim 1, comprising at least one aryl radical substituent selected from among phenyl radicals optionally substituted by at least one halogen atom, or at least one hydroxyl or nitro functional group.

28. The adamantyl-substituted biaromatic compound as defined by claim 1, comprising at least one aralkyl radical substituent selected from among benzyl or phenethyl radicals optionally substituted by at least one halogen atom, or at least one hydroxyl or nitro functional group.

29. The adamantyl-substituted biaromatic compound as defined by claim 1, comprising at least one alkenyl radical substituent selected from among those having from 2 to 5 carbon atoms and one or more sites of ethylenic unsaturation.

30. The adamantyl-substituted biaromatic compound as defined by claim 1, comprising at least one sugar residue substituent derived from glucose, galactose, mannose or glucuronic acid.

31. The adamantyl-substituted biaromatic compound as defined by claim 1, comprising at least one amino acid residue substituent derived from lysine, glycine or aspartic acid.

32. The adamantyl-substituted biaromatic compound as defined by claim 1, comprising at least one dipeptide or tripeptide residue substituent.

33. The adamantyl-substituted biaromatic compound as defined by claim 1, comprising at least one heterocyclic radical substituent selected from among piperidino, morpholino, pyrrolidino and piperazino radicals, optionally substituted in the 4-position by a $C_1$–$C_6$ alkyl or mono- or polyhydroxyalkyl radical.

34. The adamantyl-substituted biaromatic compound as defined by claim 1, comprising at least one amino alkyl radical substituent having from 1 to 6 carbon atoms.

35. The adamantyl-substituted biaromatic compound as defined by claim 1, comprising at least one alkynyl radical substituent having from 2 to 6 carbon atoms.

36. The adamantyl-substituted biaromatic compound as defined by claim 1, comprising at least one cycloaliphatic radical substituent having from 3 to 6 carbon atoms.

37. The adamantyl-substituted biaromatic compound as defined by claim 1, comprising at least one halogen atom substituent selected from among fluorine, chlorine and bromine atoms.

38. The adamantyl-substituted biaromatic compound as defined by claim 21, comprising an alkali or alkaline earth metal, zinc or amine salt.

39. The adamantyl-substituted biaromatic compound as defined by claim 1, selected from among 4-[4-(1-adamantyl)-3-methoxybenzoyloxy]benzoic acid; (E)-4-[[2-[4-(1-adamantyl)-3-hydroxyphenyl]ethenyl]]benzoic acid; (E)-4-[[2-[4-a1-Adamantyl)-3-propyloxyphenyl]ethenyl]]benzoic acid; (E) -4-[[2-[4-(1-adamantyl)-3-heptyloxyphenyl]ethenyl]]benzoic acid; (E)-4-[[2-[4-a1-Adamantyl)-3-methoxyphenyl]ethenyl]]benzoic acid; 4-[4-(1-adamantyl)-3-methoxyethoxymethoxyphenylethynyl]benzoic acid; (E)-4-[[2-[4-(1-adamantyl) -3-(5-carbamoylpentyloxy)phenyl]ethenyl]]benzoic acid; (E)-4-[[2-[4-(1-adamantyl)-3-methoxyphenyl]-1-propenyl]]benzoic acid; (E)-4-[[2-[4-(1-adamantyl)-3-(3-hydroxypropyloxy)phenyl]ethenyl]]benzoic acid; (E)-4-[[2-[4-(1-adamantyl)-3-(6-hydroxyhexyloxy)phenyl]ethenyl]]benzoic acid; 4-[[3-oxo-3-[4-(1-adamantyl)-3-methoxyphenyl]-1-propenyl]]benzoic acid; 4-[4-(1-adamantyl)-3-methoxyethoxymethoxybenzoylthio]benzoic acid; 4-[4-(1-adamantyl)-3-methoxyethoxymethoxybenzoyloxy]benzoic acid; 4-[4-(1-adamantyl)-3-methoxyethoxymethoxybenzamido]benzoic acid; (E)-4-[2-(4-(1-adamantyl)-3-methoxyethoxymethoxyphenyl)ethenyl]benzoic acid; (E)-4-[2-(4-(1-adamantyl)-3-methoxyethoxymethoxyphenyl)-1-propenyl]benzoic acid; (Z)-4-[2-(4-(1-adamantyl) -3-methoxyethoxymethoxyphenyl)-1-propenyl]benzoic acid; 4-[4-(1-adamantyl)-3-methoxyethoxymethoxybenzoylmethyloxy]benzoic acid; 4-[[3-oxo-3-[4-(1-adamantyl)-3-methoxyethoxymethoxyphenyl]-1-propynyl]]benzoic acid; 4-[[3-hydroxy-3-[4-(1-adamantyl)-3-methoxyethoxymethoxyphenyl]-1-propynyl]]benzoic acid; (E)-4-[[3-oxo-3-[4-(1-adamantyl)-3-methoxyethoxymethoxyphenyl]-1-propenyl]]benzoic acid; 4-[[3-hydroxy-3-[4-(1-adamantyl)-3-methoxyethoxymethoxyphenyl]-1-propenyl]]benzoic acid; allyl 4-[4-(1-adamantyl)-3-methoxyethoxymethoxythiobenzamido]benzoate; 4-[[3-hydroxy-3-[4-(1-adamantyl)-3-methoxyphenyl]-1-propynyl]]benzoic acid; 2-hydroxy-4-[[3-hydroxy-3-[4-(1-adamantyl)-3-methoxyphenyl]-1-propynyl]]benzoic acid; 2-hydroxy-4-[[3-hydroxy-3-[4-(1-adamantyl)-3-methoxyethoxymethoxyphenyl]-1-propynyl]]benzoic acid; 4-[[3-hydroxy-3-[4-(1-adamantyl)-3-methoxyethoxymethoxyphenyl]-1-propynyl]]benzaldehyde; 4-[[3-hydroxy-3-[4-(1-adamantyl)-3-methoxyethoxymethoxyphenyl]-1-propynyl]]benzenemethanol; N-ethyl-4-[4-(1-adamantyl)-3-methoxyethoxymethoxyphenylethynyl]benzamide; N-(4-hydroxyphenyl)-4-[4-(1-adamantyl)-3-methoxyethoxymethoxyphenylethynyl]benzamide; 4-[4-(1-adamantyl)-3-methoxyethoxymethoxyphenylethynyl]phenol.

40. The adamantyl-substituted biaromatic compound as defined by claim 1, wherein formula (I), at least one of the following conditions exist:
$R_1$ is the radical —COO—$R_7$ or —CO—$R_6$;
$R_3$ is the radical —Y—$(CH_2)_p$—Y$(CH_2)_q$—$R_8$, —$(CH_2)_p$—$(Y)_n$—$(CH_2)_q$—$R_8$ or —Y—$(CH_2)_q$—$R_8$;
X is a bridging radical of formula (a), (h), (i), (j), (k) or (m); and
Ar is a radical of formula (a') or (b').

41. A pharmaceutical composition of matter, comprising a therapeutically effective amount of an adamantyl-substituted biaromatic compound as defined by claim 1, or pharmaceutically acceptable derivative or isomer thereof, and a pharmaceutically acceptable vehicle, carrier or diluent therefor.

42. The pharmaceutical composition as defined by claim 41, further comprising a retinoid compound, a D vitamin or derivative thereof, a corticosteroid, an anti-free radical agent, an α-hydroxy or α-keto acid or derivative thereof, an ion channel blocker, or combination thereof.

43. The pharmaceutical composition as defined by claim 41, comprising a tablet, a capsule, a syrup, a dragee, a suspension, an elixir, a solution, a powder, granules, an emulsion, microspheres, nanospheres, lipid vesicles, polymeric vesicles, or an injectable.

44. The pharmaceutical composition as defined by claim 41, comprising an ointment, a cream, a milk, a salve, an impregnated pad, a gel, a spray, or a lotion.

45. The pharmaceutical composition as defined by claim 41, adopted for topical administration.

46. The pharmaceutical composition as defined by claim 41, adopted for systemic administration.

47. The pharmaceutical composition as defined by claim 41, comprising from 0.001% to 5% by weight of said adamantyl-substituted biaromatic compound, or derivative or isomer thereof.

48. A method of treating a dermatological, rheumatic, respiratory, cardiovascular, bone or ophthalmologic disorder in a mammalian organism in need of such treatment, comprising administering to such organism a therapeutically effective amount of the pharmaceutical composition as defined by claim 41.

49. A method for treating osteoporosis in a mammalian organism in need of such treatment, comprising administering to such organism a therapeutically effective amount of the pharmaceutical composition as defined by claim 41.

50. The method as defined by claim 48, comprising administering to such organism a daily dose of said adamantyl-substituted biaromatic compound of about 0.01 mg/kg to 100 mg/kg of body weight thereof.

51. A cosmetic composition of matter, comprising a cosmetically effective amount of an adamantyl-substituted biaromatic compound as defined by claim 1, or cosmetically acceptable derivative or isomer thereof, and a cosmetically acceptable vehicle, carrier or diluent therefor.

52. The cosmetic composition as defined by claim 51, comprising a cream, a milk, a lotion, a gel, an ointment, microspheres, nanospheres, lipid vesicles, polymeric vesicles, a soap, or a shampoo.

53. The cosmetic composition as defined by claim 51, comprising from 0.001% to 3% by weight of said adamantyl-substituted biaromatic compound, or derivative or isomer thereof.

54. The cosmetic composition as defined by claim 51, further comprising a retinoid compound, a D vitamin or derivative thereof, a corticosteroid, an anti-free radical agent, an u-hydroxy or u-keto acid or derivative thereof, an ion channel blocker, or combination thereof.

55. The pharmaceutical composition as defined by claim 51, further comprising a wetting agent, a depigmenting agent, a moisturizing agent, an emollient, an antiseborrhoeic or antiacne agent, an antibiotic, an antifungal agent, a hair regrowth promoter, a non-steroidal anti-inflammatory agent, a carotenoid, an anti-psoriatic agent, 5,5,11,14-eicosatetraynoic or 5,8,11-eicosatrynoic acid or ester or amide thereof, or combination thereof.

56. The pharmaceutical composition as defined by claim 51, further comprising a taste- or flavor-enhancing agent, a preservative, a stabilizer, a moisture regulating agent, a pH regulating agent, an osmotic pressure modifying agent, an emulsifying agent, a UV-A or UV-B screening agent, an antioxidant, or combination thereof.

57. The cosmetic composition by claim 51, further comprising a wetting agent, a depigmenting agent, a moisturizing agent, an emollient, an antiseborrhoeic or antiacne agent, an antibiotic, an antifungal agent, a hair regrowth promoter, a non-steroidal anti-inflammatory agent, a carotenoid, an anti-psoriatic agent, 5,8,11,14-eicosatetraynoic or 5,8,11-eicosatrynoic acid or ester or amide thereof, or combination thereof.

58. The cosmetic composition as defined by claim 51, further comprising a taste- or flavor-enhancing agent, a preservative, a stabilizer, a moisture regulating agent, a pH regulating agent, an osmotic pressure modifying agent, an emulsifying agent, a UV-A or UV-B screening agent, an antioxidant, or combination thereof.

* * * * *

UNITED STATES PATENT AND TRADEMARK OFFICE
CERTIFICATE OF CORRECTION

Figure 2:
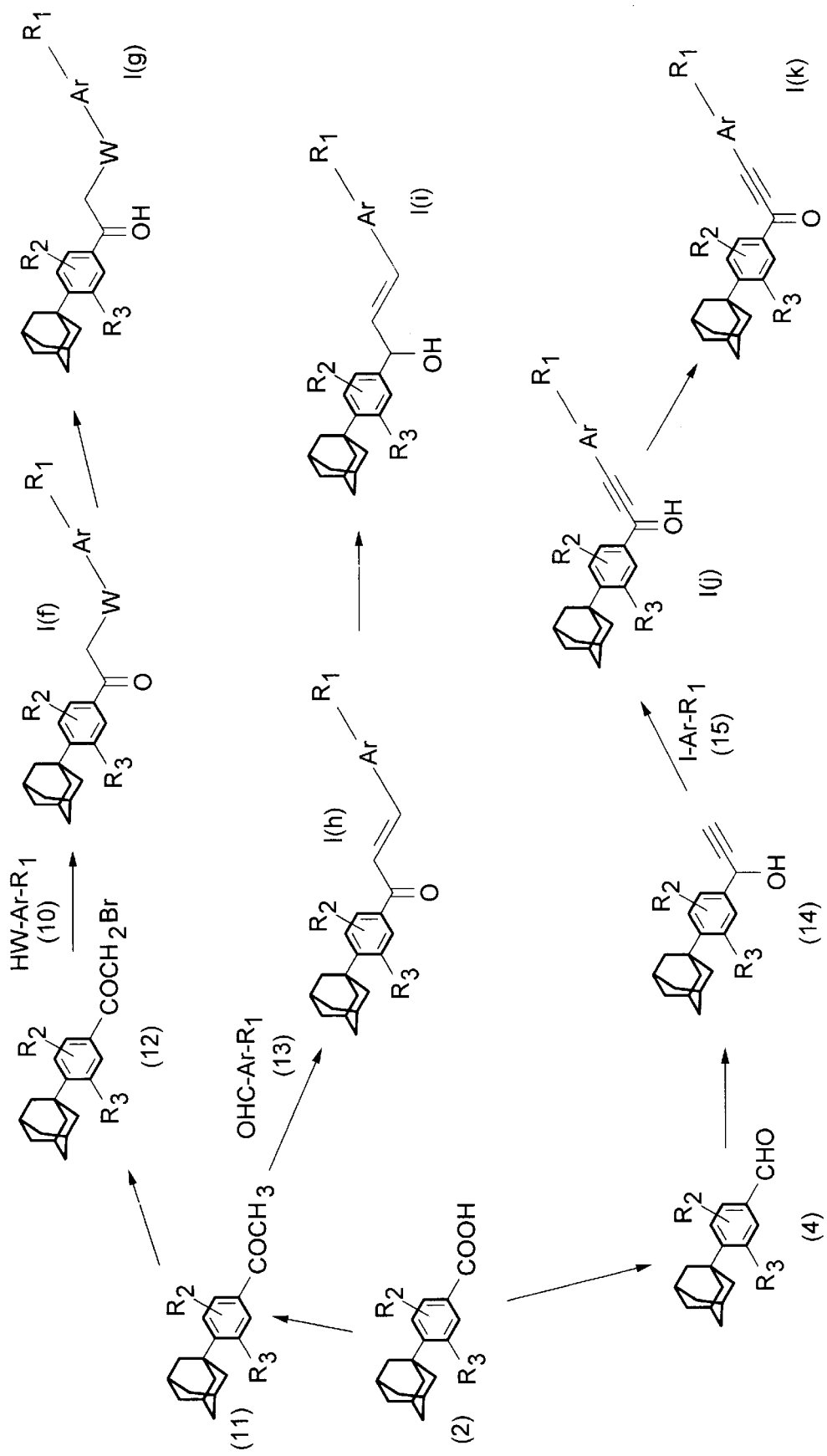
Figure 3:
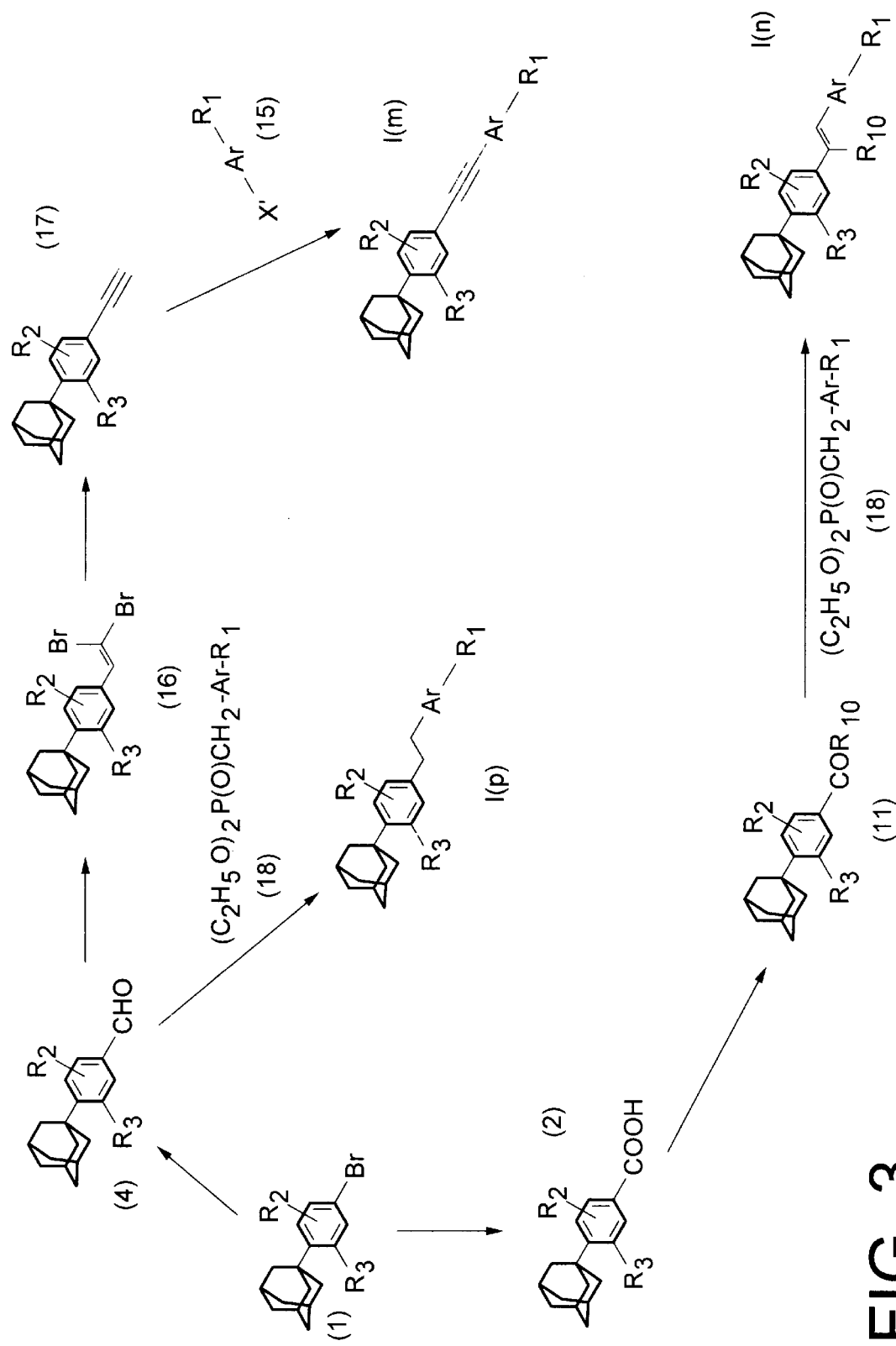
Figure 4:
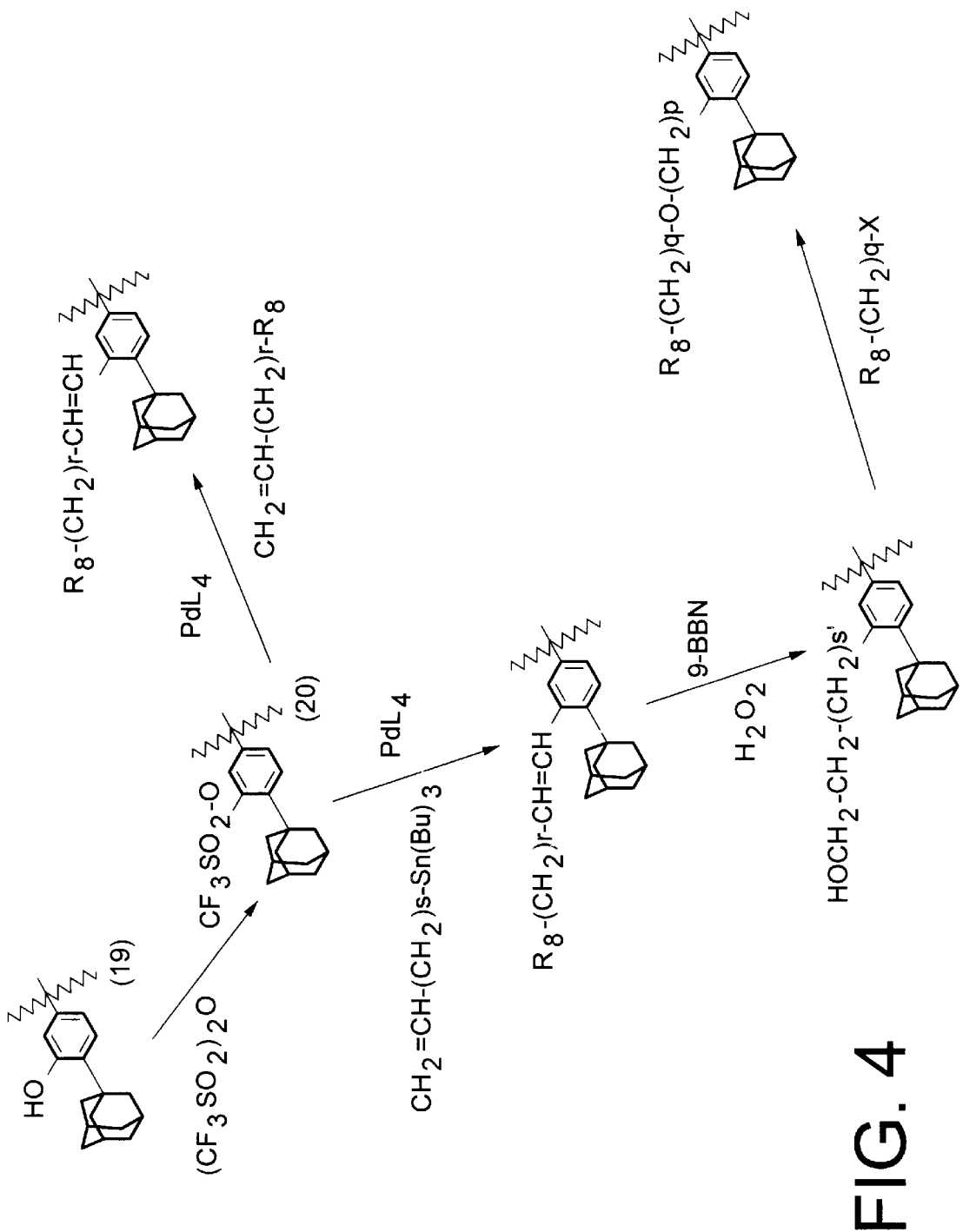
Figure 2:
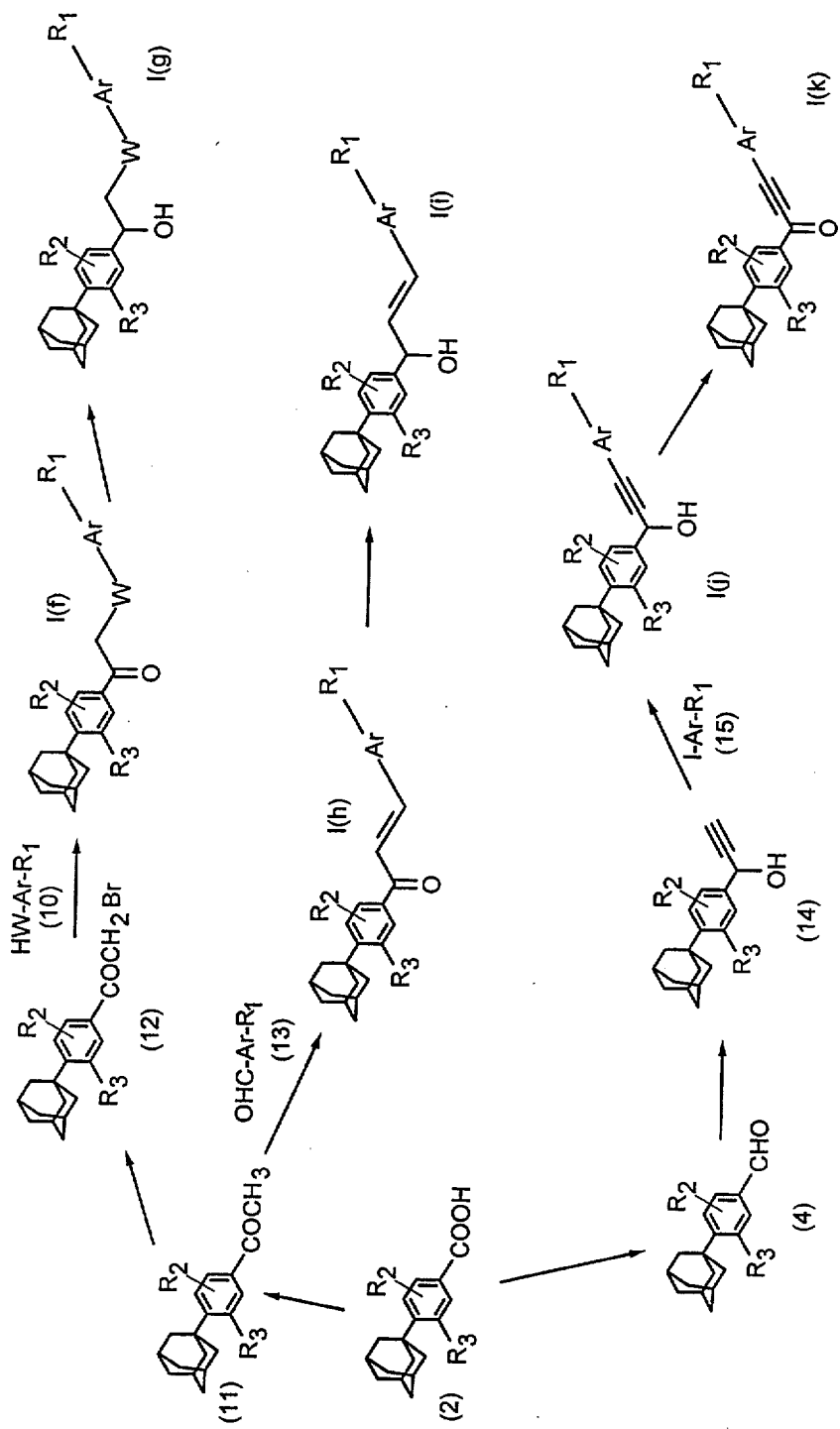
Figure 4:
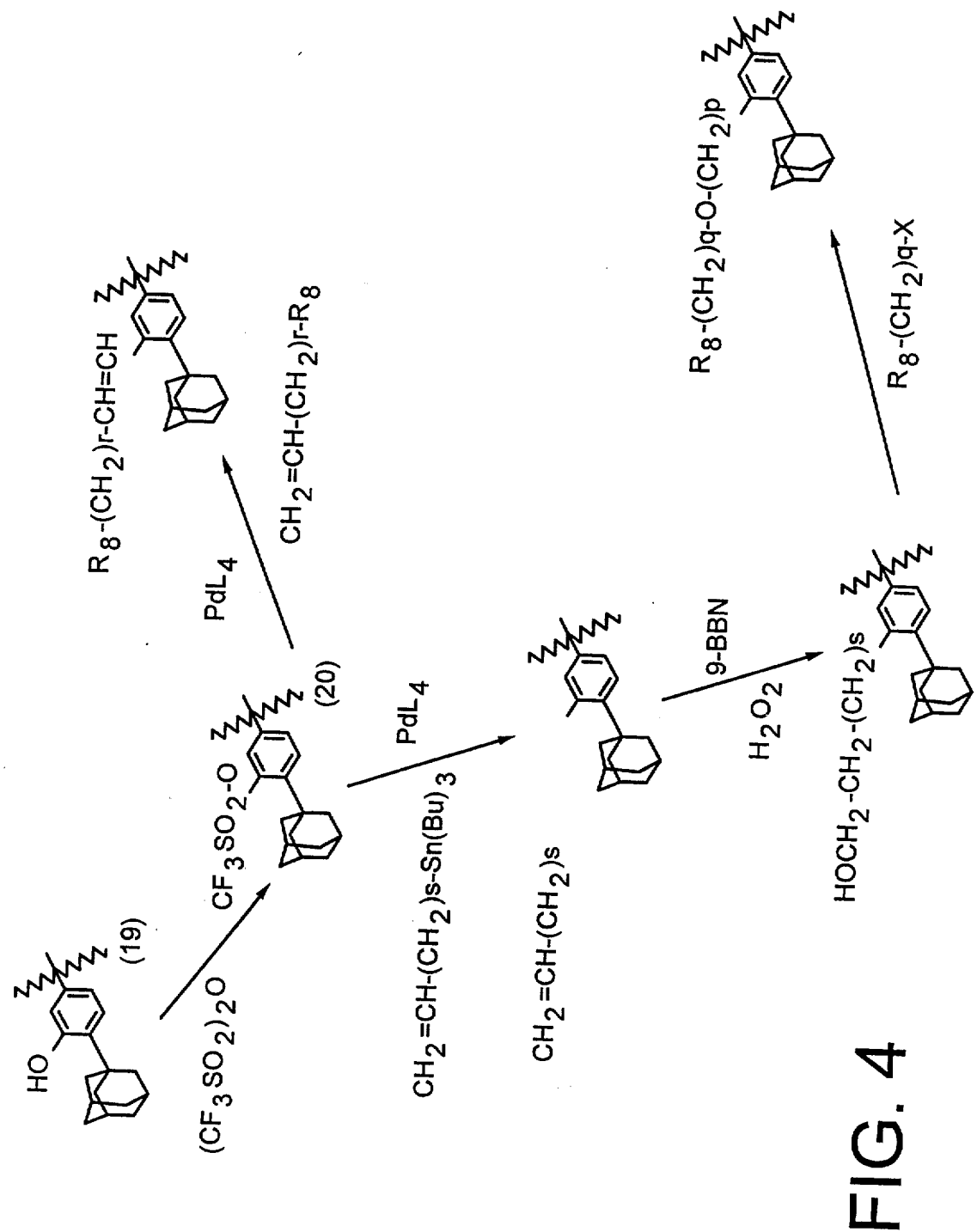

PATENT NO. : 5,877,342
DATED : March 2, 1999
INVENTOR(S) : Jean-Michel Bernardon et al It is certified that error appears in the above-identified patent and that said Letters Patent is hereby corrected as shown below:

Drawing Sheets, consisting of Figs. 2 and 4, should be deleted to be replaced with Drawing Sheets, consisting of Figs. 2 and 4, as shown on the attached page.

Column 14, please delete lines 39-54.

Column 29, lines 38 and 40, please change "[4-a1-adamantyl)" to --[4-(1-adamantyl)--.

Column 31, line 17, please change "u-hydroxy or u-keto" to --α-hydroxy or α-keto--.

Signed and Sealed this

Twelfth Day of September, 2000

Attest:

Q. TODD DICKINSON

*Attesting Officer*    *Director of Patents and Trademarks*